(12) United States Patent
Kemper et al.

(10) Patent No.: US 12,213,715 B2
(45) Date of Patent: *Feb. 4, 2025

(54) ON-DEMAND IMPLANT CUSTOMIZATION IN A SURGICAL SETTING

(71) Applicant: Stryker European Operations Limited, Carrigtwohill (IE)

(72) Inventors: Jakob Kemper, Heemstede (NL); Bernd Robioneck, Plön (DE); Manoj Kumar Singh, Mahwah, NJ (US); Peter Sterrantino, Jacksonville, FL (US)

(73) Assignee: Stryker European Operations Limited, Carrigtwohill (IE)

( * ) Notice: Subject to any disclaimer, the term of this patent is extended or adjusted under 35 U.S.C. 154(b) by 303 days.

This patent is subject to a terminal disclaimer.

(21) Appl. No.: 17/829,505

(22) Filed: Jun. 1, 2022

(65) Prior Publication Data
US 2022/0287753 A1     Sep. 15, 2022

Related U.S. Application Data

(63) Continuation of application No. 16/387,079, filed on Apr. 17, 2019, now Pat. No. 11,376,054.
(Continued)

(51) Int. Cl.
*A61B 17/88* (2006.01)
*A61B 34/10* (2016.01)
(Continued)

(52) U.S. Cl.
CPC .......... *A61B 17/8863* (2013.01); *A61B 34/10* (2016.02); *A61F 2/30942* (2013.01);
(Continued)

(58) Field of Classification Search
CPC ..... A61F 2/30942; A61B 17/80; A61B 17/58; A61B 2034/108
See application file for complete search history.

(56) References Cited

U.S. PATENT DOCUMENTS 5,298,115 A    3/1994   Leonard
6,015,289 A    1/2000   Andreiko et al.
(Continued)

OTHER PUBLICATIONS

European Search Report issued in Appln. No. 19789410.8 mailed Nov. 30, 2021 (2 pages).
(Continued)

*Primary Examiner* — Andrew Yang
(74) *Attorney, Agent, or Firm* — Lerner David LLP

(57) ABSTRACT

Disclosed herein are apparatuses and methods for intraoperative on-demand implant customization in a surgical setting. An apparatus may include a storage portion, an implant customization portion and an interface. The storage portion may house implant blanks and implant accessories. The implant customization portion may customize the implant blanks. The interface may be configured to receive implant customization information and utilize the same to intraoperatively manipulate the implant blank to a patient-specific implant within a sterile environment. A method to customize an implant in a surgical care environment may include the steps of obtaining information related to the implant location, selecting an implant blank based on the information, and customizing the implant blank in a surgical care setting with a customization apparatus.

20 Claims, 39 Drawing Sheets

Related U.S. Application Data

(60) Provisional application No. 62/658,925, filed on Apr. 17, 2018.

(51) Int. Cl.
*A61F 2/30* (2006.01)
*G06F 30/00* (2020.01)

(52) U.S. Cl.
CPC ........ *G06F 30/00* (2020.01); *A61B 2034/102* (2016.02); *A61B 2034/105* (2016.02); *A61B 2034/108* (2016.02); *A61F 2002/3096* (2013.01)

(56) References Cited

U.S. PATENT DOCUMENTS

| | | |
|---|---|---|
| 6,205,411 B1 | 3/2001 | DiGioia, III et al. |
| 6,459,948 B1 | 10/2002 | Ateshian et al. |
| 6,520,964 B2 | 2/2003 | Tallarida et al. |
| 6,679,917 B2 | 1/2004 | Ek |
| 6,772,026 B2 | 8/2004 | Bradbury et al. |
| 7,383,164 B2 | 6/2008 | Aram et al. |
| 7,468,075 B2 | 12/2008 | Lang et al. |
| 7,603,192 B2 | 10/2009 | Martin et al. |
| 7,618,462 B2 | 11/2009 | Ek |
| 7,747,305 B2 | 6/2010 | Dean et al. |
| 7,925,324 B2 | 4/2011 | Maier |
| 7,957,831 B2 | 6/2011 | Isaacs |
| 7,983,777 B2 | 7/2011 | Melton et al. |
| 8,064,660 B2 | 11/2011 | Leow et al. |
| 8,108,025 B2 | 1/2012 | Csavoy et al. |
| 8,234,097 B2 | 7/2012 | Steines et al. |
| 8,246,663 B2 | 8/2012 | Lovald et al. |
| 8,281,638 B2 | 10/2012 | Metzger |
| 8,311,306 B2 | 11/2012 | Pavlovskaia et al. |
| 8,311,791 B1 | 11/2012 | Avisar |
| 8,327,519 B2 | 12/2012 | Linares |
| 8,337,507 B2 | 12/2012 | Lang et al. |
| 8,377,073 B2 | 2/2013 | Wasielewski |
| 8,407,067 B2 | 3/2013 | Uthgenannt et al. |
| 8,532,807 B2 | 9/2013 | Metzger |
| 8,538,117 B2 | 9/2013 | Najarian et al. |
| 8,549,888 B2 | 10/2013 | Isaacs |
| 8,556,983 B2 | 10/2013 | Bojarski et al. |
| 8,617,242 B2 | 12/2013 | Philipp |
| 8,655,468 B2 | 2/2014 | Bake et al. |
| 8,690,945 B2 | 4/2014 | Fitz et al. |
| 8,702,686 B2 | 4/2014 | Geebelen et al. |
| 8,706,285 B2 | 4/2014 | Narainasamy et al. |
| 8,709,089 B2 | 4/2014 | Lang et al. |
| 8,735,773 B2 | 5/2014 | Lang |
| 8,744,819 B2 | 6/2014 | Rodriguez Y Baena |
| 8,768,028 B2 | 7/2014 | Lang et al. |
| 8,807,999 B2 | 8/2014 | Kuo et al. |
| 8,831,302 B2 | 9/2014 | Mahfouz |
| 8,843,229 B2 | 9/2014 | Vanasse et al. |
| 8,868,226 B2 | 10/2014 | Lal |
| 8,939,982 B2 | 1/2015 | Chellaoui |
| 8,983,813 B2 | 3/2015 | Miles et al. |
| 8,984,731 B2 | 3/2015 | Broeck et al. |
| 8,989,460 B2 | 3/2015 | Mahfouz |
| 8,990,052 B2 | 3/2015 | Lavallee et al. |
| 9,009,012 B2 | 4/2015 | Bake et al. |
| 9,015,922 B2 | 4/2015 | Ganey |
| 9,020,788 B2 | 4/2015 | Lang et al. |
| 9,055,953 B2 | 6/2015 | Lang et al. |
| 9,056,017 B2 | 6/2015 | Kotlus |
| 9,078,755 B2 | 7/2015 | Mahfouz |
| 9,186,254 B2 | 11/2015 | Fitz et al. |
| 9,208,263 B2 | 12/2015 | Pavlovskaia et al. |
| 9,233,001 B2 | 1/2016 | Miles et al. |
| 9,250,620 B2 | 2/2016 | Kotlus |
| 9,259,291 B2 | 2/2016 | Gantes |
| 9,275,192 B2 | 3/2016 | Kang et al. |
| 9,320,604 B2 | 4/2016 | Miles et al. |
| 9,326,780 B2 | 5/2016 | Wong et al. |
| 9,333,085 B2 | 5/2016 | Fitz et al. |
| 9,345,548 B2 | 5/2016 | Schoenefeld et al. |
| 9,345,551 B2 | 5/2016 | Mahfouz |
| 9,364,294 B2 | 6/2016 | Razzaque et al. |
| 9,375,303 B1 | 6/2016 | Cook et al. |
| 9,381,072 B2 | 7/2016 | Furrer et al. |
| 9,387,083 B2 | 7/2016 | Al Hares et al. |
| 9,398,936 B2 | 7/2016 | Razzaque et al. |
| 9,408,686 B1 | 8/2016 | Miller et al. |
| 9,408,698 B2 | 8/2016 | Miles et al. |
| 9,439,767 B2 | 9/2016 | Bojarski et al. |
| 9,452,050 B2 | 9/2016 | Miles et al. |
| 9,474,582 B2 | 10/2016 | Musuvathy et al. |
| 9,495,483 B2 | 11/2016 | Steines et al. |
| 9,517,134 B2 | 12/2016 | Lang |
| 9,532,788 B2 | 1/2017 | Jordan et al. |
| 9,554,910 B2 | 1/2017 | Vanasse et al. |
| 9,573,322 B2 | 2/2017 | Wasielewski |
| 9,603,670 B2 | 3/2017 | Brianza et al. |
| 9,629,698 B2 | 4/2017 | Lior et al. |
| 9,629,705 B2 | 4/2017 | Douthitt et al. |
| 9,636,181 B2 | 5/2017 | Isaacs |
| 9,646,113 B2 | 5/2017 | Park et al. |
| 9,662,214 B2 | 5/2017 | Li et al. |
| 10,646,259 B2 | 5/2020 | McGahan et al. |
| 2002/0007294 A1 | 1/2002 | Bradbury et al. |
| 2003/0055435 A1 | 3/2003 | Barrick |
| 2003/0055502 A1 | 3/2003 | Lang et al. |
| 2004/0009459 A1 | 1/2004 | Anderson et al. |
| 2004/0068187 A1 | 4/2004 | Krause et al. |
| 2004/0115586 A1 | 6/2004 | Andreiko et al. |
| 2004/0243481 A1 | 12/2004 | Bradbury et al. |
| 2005/0262911 A1 | 12/2005 | Dankowicz et al. |
| 2006/0136058 A1 | 6/2006 | Pietrzak |
| 2006/0257379 A1 | 11/2006 | Giordano et al. |
| 2007/0118243 A1 | 5/2007 | Schroeder et al. |
| 2008/0195216 A1 | 8/2008 | Philipp |
| 2008/0257363 A1 | 10/2008 | Schoenefeld et al. |
| 2009/0087276 A1 | 4/2009 | Rose |
| 2009/0151736 A1 | 6/2009 | Belcher et al. |
| 2009/0254097 A1 | 10/2009 | Isaacs |
| 2009/0254326 A1 | 10/2009 | Isaacs |
| 2009/0263764 A1 | 10/2009 | Berckmans, III et al. |
| 2010/0329530 A1 | 12/2010 | Lang et al. |
| 2011/0004317 A1 | 1/2011 | Hacking et al. |
| 2011/0008754 A1 | 1/2011 | Bassett et al. |
| 2011/0184526 A1 | 7/2011 | White et al. |
| 2011/0208256 A1 | 8/2011 | Zuhars |
| 2012/0066892 A1 | 3/2012 | Lang et al. |
| 2012/0072185 A1 | 3/2012 | Lang et al. |
| 2012/0116203 A1 | 5/2012 | Vancraen et al. |
| 2012/0141034 A1 | 6/2012 | Iannotti et al. |
| 2012/0191420 A1 | 7/2012 | Bojarski et al. |
| 2012/0251980 A1 | 10/2012 | Bassett et al. |
| 2013/0066319 A1 | 3/2013 | Aram et al. |
| 2013/0103363 A1 | 4/2013 | Lang et al. |
| 2013/0110471 A1 | 5/2013 | Lang et al. |
| 2013/0199259 A1 | 8/2013 | Smith |
| 2013/0211531 A1 | 8/2013 | Steines et al. |
| 2013/0245803 A1 | 9/2013 | Lang |
| 2013/0345757 A1 | 12/2013 | Stad |
| 2014/0005792 A1 | 1/2014 | Lang et al. |
| 2014/0019110 A1 | 1/2014 | Otto et al. |
| 2014/0086780 A1 | 3/2014 | Miller et al. |
| 2014/0096369 A1 | 4/2014 | Matsumoto et al. |
| 2014/0109384 A1 | 4/2014 | Lang |
| 2014/0200902 A1 | 7/2014 | Aram et al. |
| 2014/0228860 A1 | 8/2014 | Steines et al. |
| 2014/0244220 A1 | 8/2014 | Mckinnon et al. |
| 2014/0250676 A1 | 9/2014 | Lang et al. |
| 2014/0259629 A1 | 9/2014 | Dion et al. |
| 2014/0276854 A1 | 9/2014 | Schoenefeld et al. |
| 2014/0371863 A1 | 12/2014 | Vanasse et al. |
| 2015/0051650 A1 | 2/2015 | Verstreken et al. |
| 2015/0088293 A1 | 3/2015 | Metzger |
| 2015/0112443 A1 | 4/2015 | Gelaude |
| 2015/0119987 A1 | 4/2015 | Davignon et al. |
| 2015/0134017 A1 | 5/2015 | Chellaoui |

(56) References Cited

U.S. PATENT DOCUMENTS

| | | |
|---|---|---|
| 2015/0182314 A1 | 7/2015 | Morales et al. |
| 2015/0220682 A1 | 8/2015 | Netravali et al. |
| 2015/0227679 A1 | 8/2015 | Kamer et al. |
| 2015/0297350 A1 | 10/2015 | Robichaud et al. |
| 2015/0305878 A1 | 10/2015 | O'Neil et al. |
| 2015/0313652 A1 | 11/2015 | Burckhardt et al. |
| 2015/0320471 A1 | 11/2015 | Crawford et al. |
| 2015/0320508 A1 | 11/2015 | White et al. |
| 2015/0324114 A1 | 11/2015 | Hurley et al. |
| 2015/0328004 A1 | 11/2015 | Mafhouz |
| 2015/0342739 A1 | 12/2015 | Mahfouz |
| 2015/0351916 A1 | 12/2015 | Kosarek et al. |
| 2016/0015465 A1 | 1/2016 | Steines et al. |
| 2016/0022370 A1 | 1/2016 | Pavlovskaia et al. |
| 2016/0038161 A1 | 2/2016 | Gibson |
| 2016/0045317 A1 | 2/2016 | Lang et al. |
| 2016/0058510 A1 | 3/2016 | Blice et al. |
| 2016/0106518 A1 | 4/2016 | Choi et al. |
| 2016/0166392 A1 | 6/2016 | Vanasse et al. |
| 2016/0206331 A1 | 7/2016 | Fitz et al. |
| 2016/0213343 A1 | 7/2016 | Barth et al. |
| 2016/0217268 A1 | 7/2016 | Otto et al. |
| 2016/0242857 A1 | 8/2016 | Scholl |
| 2016/0242931 A1 | 8/2016 | Wong et al. |
| 2016/0256279 A1 | 9/2016 | Sanders et al. |
| 2016/0278927 A1 | 9/2016 | Cook et al. |
| 2016/0296321 A1 | 10/2016 | Roels et al. |
| 2016/0302870 A1 | 10/2016 | Wilkinson et al. |
| 2016/0317311 A1 | 11/2016 | Meridew |
| 2016/0324581 A1 | 11/2016 | Bojarski et al. |
| 2016/0324642 A1 | 11/2016 | Maria De Peppo |
| 2016/0331463 A1 | 11/2016 | Notzli et al. |
| 2016/0331466 A1 | 11/2016 | Aram et al. |
| 2016/0331467 A1 | 11/2016 | Slamin et al. |
| 2016/0338776 A1 | 11/2016 | Jaramaz et al. |
| 2016/0338778 A1 | 11/2016 | Zuhars |
| 2017/0000569 A1 | 1/2017 | Mahfouz |
| 2017/0000614 A1 | 1/2017 | Mahfouz |
| 2017/0000615 A1 | 1/2017 | Mahfouz |
| 2017/0014169 A1 | 1/2017 | Dean et al. |
| 2017/0056086 A1 | 3/2017 | Kostrzewski et al. |
| 2017/0056179 A1 | 3/2017 | Lorio |
| 2017/0056180 A1 | 3/2017 | Schmieding |
| 2017/0056183 A1 | 3/2017 | Steines et al. |
| 2017/0057169 A1 | 3/2017 | Grbic et al. |
| 2017/0065347 A1 | 3/2017 | Bojarski et al. |
| 2017/0100253 A1 | 4/2017 | Bake et al. |
| 2017/0105841 A1 | 4/2017 | Vanasse et al. |
| 2017/0119531 A1 | 5/2017 | Bojarski et al. |
| 2017/0143494 A1 | 5/2017 | Mahfouz |
| 2017/0143495 A1 | 5/2017 | Dunn et al. |
| 2017/0360493 A1 | 12/2017 | Zucker et al. |

OTHER PUBLICATIONS

International Search Report including the Written Opinion from Application No. PCT/US2019/27877 mailed Jul. 1, 2019, 16 pages.

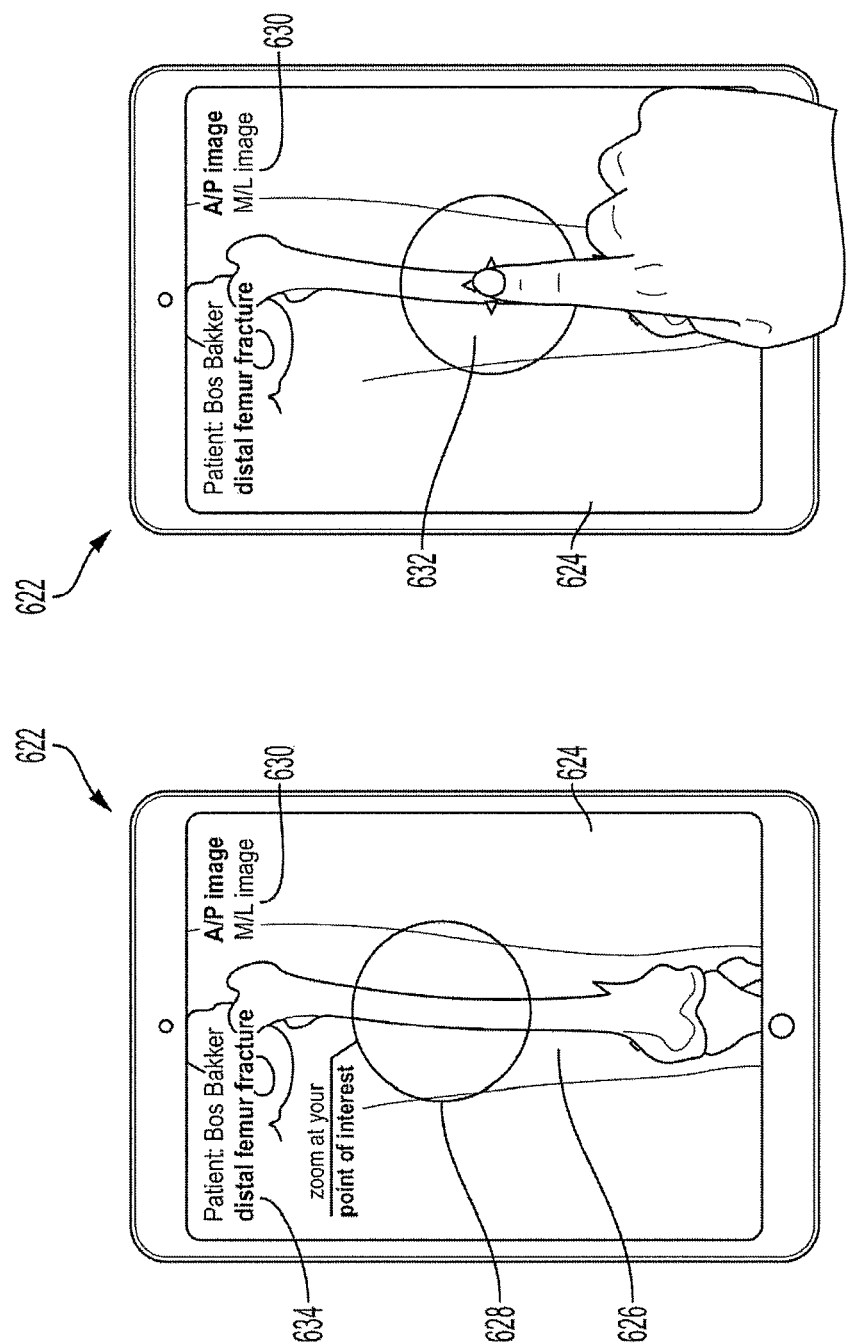

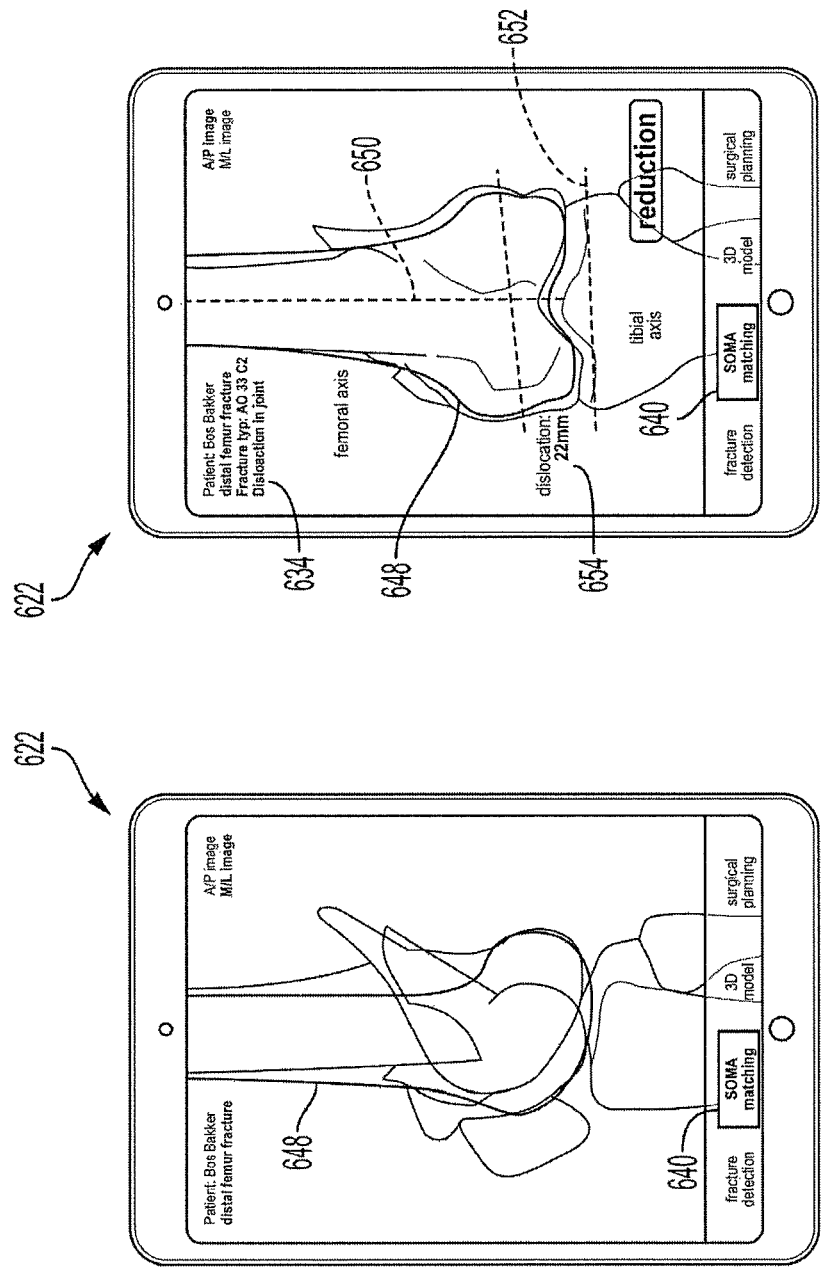

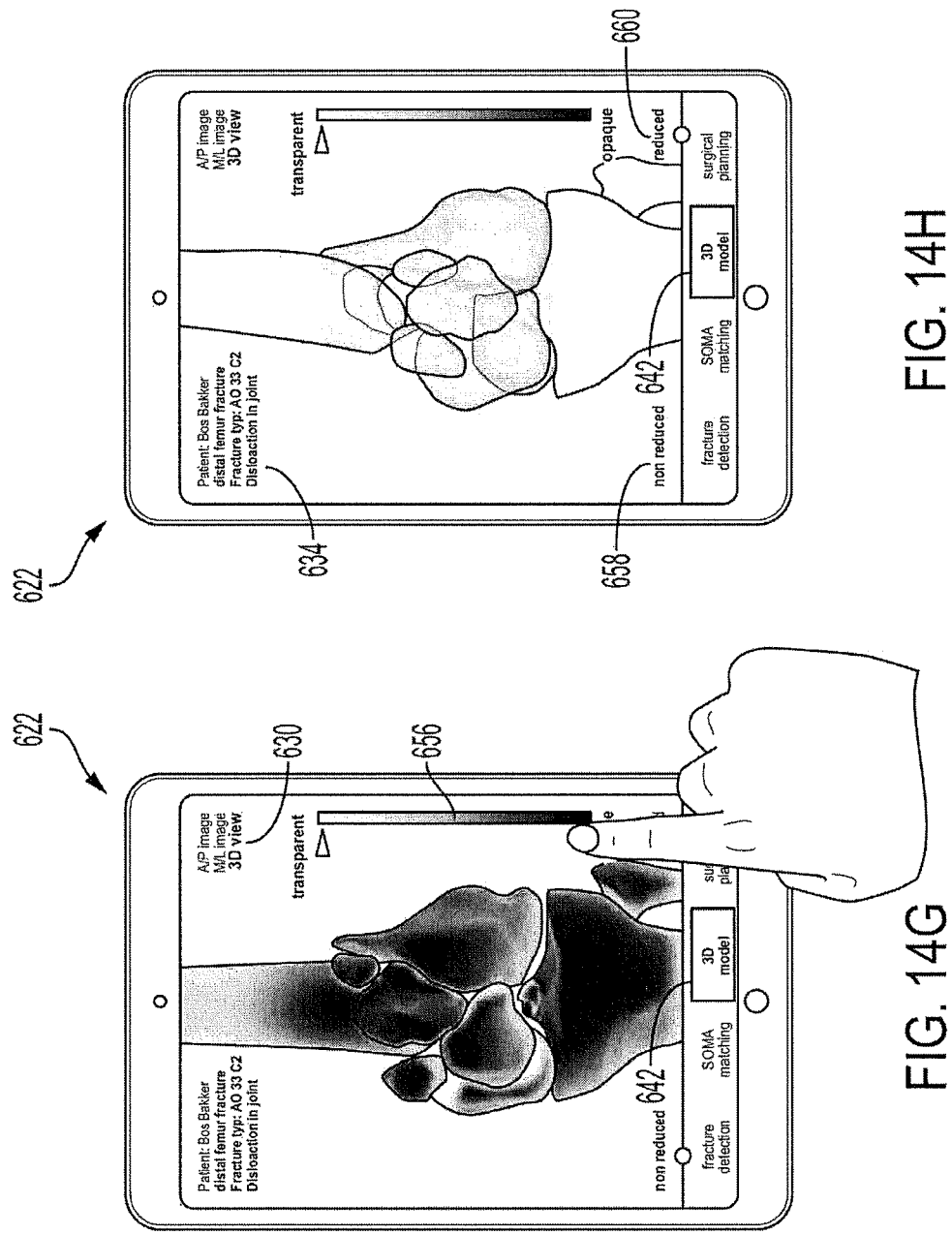

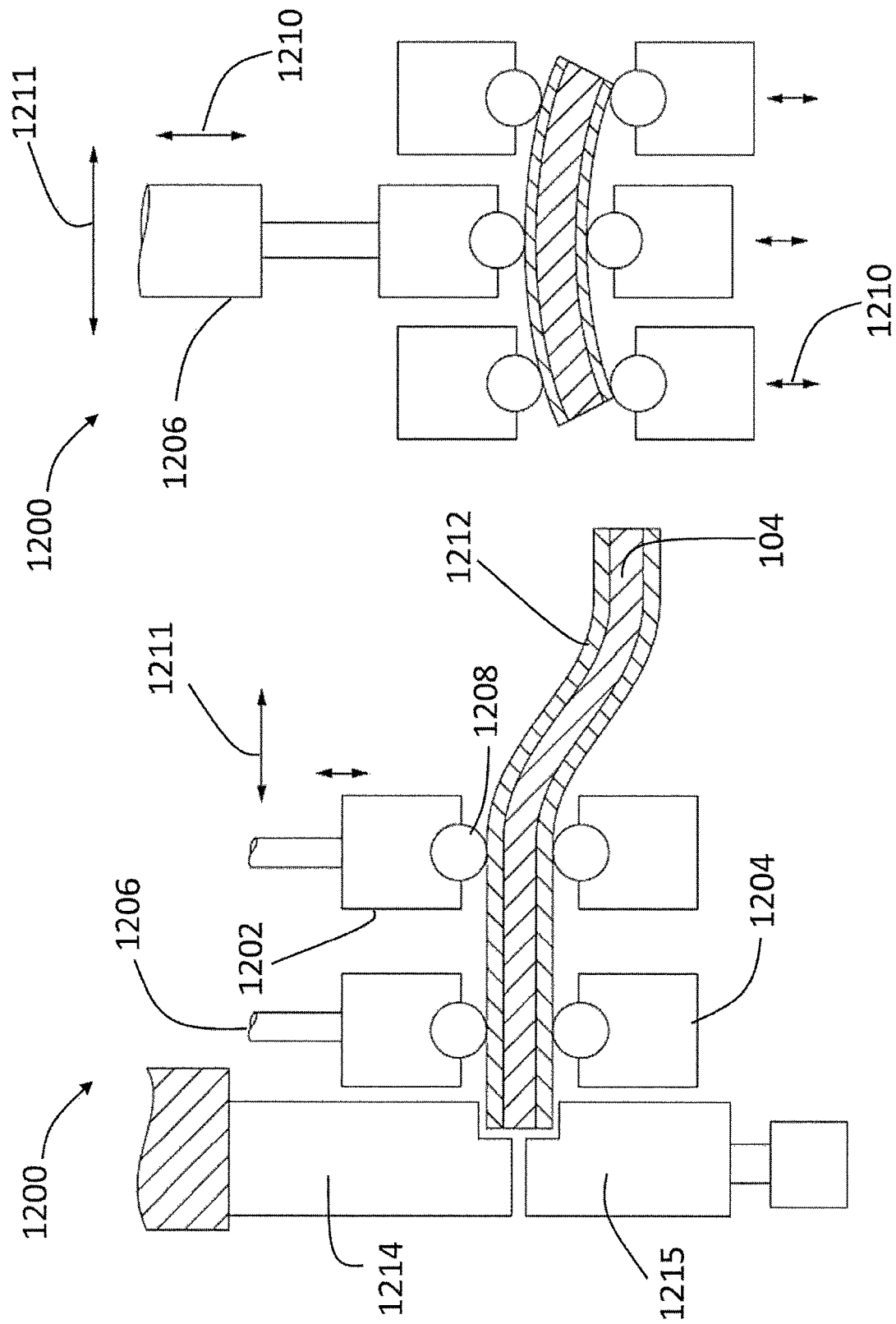

ON-DEMAND IMPLANT CUSTOMIZATION IN A SURGICAL SETTING

CROSS-REFERENCE TO RELATED APPLICATIONS

The application is a continuation of U.S. application Ser. No. 16/387,079, filed on Apr. 17, 2019, which claims the benefit of the filing date of U.S. Provisional Patent Application No. 62/658,925 filed Apr. 17, 2018, the disclosures of which are hereby incorporated herein by reference.

FIELD OF THE INVENTION

The present invention generally relates to an apparatus and a method for implant customization, and in particular, relates to an apparatus and a method for intraoperative implant customization in a surgical setting.

BACKGROUND OF THE INVENTION

Medical implants are generally fabricated as standard (patient-independent) or customized (patient-specific) implants. Customized implants are generally preferred because they are designed for patient-specific needs and consequently offer improved performance Patient-independent implants, however, are easier and cheaper to manufacture but may not address patient-specific needs. Patient-independent implants are designed and fabricated in standard sizes, and may not precisely match the anatomy or the needs of a specific patient. Surgeons utilizing these standard sizes may often be required to spend considerable time and effort to sculpt and modify these implants intraoperatively to tailor the standard implants for the specific needs of a patient. Surgeons may utilize table-top benders, implant cutters and various other tools to customize these standard implants. However, intraoperative customization performed in this manner is generally imprecise and will often depend on the surgeon's skill. Fabricating patient-independent implants to cover the needs of a diverse patient population is impractical and cost prohibitive because of the wide variation in patient anatomy and patient-specific needs.

Patient-specific implants are fabricated to meet the unique requirements of a specific patient. These unique requirements are first assessed and then used to design and fabricate the patient-specific implant. Significant time may be required to fabricate these patient-specific custom implants. Furthermore, fabrication of custom implants is performed in a manufacturing facility away from the surgical facility due to the specialized machining requirements and the need to maintain sterile conditions within the surgical space. Consequently, there may be long lead times before patients can be implanted with customized implants as these implants have to designed, fabricated, and shipped back to the surgical facility. Long lead times may not be practical for certain surgical procedures such as fractures. Additionally, customized implants are significantly more expensive than standard implants as they have to be customized, shipped and sterilized, and there are none of the savings typically associated with bulk manufacturing.

Therefore, there exists a need for an apparatus and a method for intraoperative on-demand implant customization in a surgical setting.

BRIEF SUMMARY OF THE INVENTION

Disclosed herein are apparatuses and methods for intraoperative on-demand implant customization in a surgical setting. An apparatus may include various components such as a storage portion, an implant customization portion and an interface. All components may be located within a sterile environment. The storage portion may house implant blanks and various implant accessories. The implant customization portion may include mechanisms to customize the implant blanks. The interface may be configured to receive implant customization information from various sources, analyze this information, and utilize the same to intraoperatively manipulate the implant blank to a patient-specific implant within a sterile environment. The apparatus may include various levels of automation and customization depending on the type of implant, the level of customization required, and the location of the apparatus.

In a first aspect of the present invention, an apparatus for customizing an implant is provided. The apparatus may include a storage portion, an implant customization portion and an interface configured to receive implant customization information. The storage portion may house one or more blank implants. The implant customization portion may customize the implant blanks. The apparatus may be located in a sterile environment such that the implant customization information may be used by the customization portion to intraoperatively manipulate the implant blank to a patient-specific implant within the sterile environment.

In accordance with the first aspect, the storage portion and the implant customization portion may be sterile such that the implant blanks may remain sterile during and after customization.

The implant customization portion may include a bending mechanism such that the implant blank may be bent to form the patient-specific implant. The bending mechanism may include a series of movable elements. A distal end of at least one element may be configured to be translated by an actuator such that the distal ends of the movable elements define a profile of the patient-specific implant. The bending mechanism may include a first row of movable elements on a first side of the patient-specific implant and a second row of movable elements on a second side of the patient-specific implant. The bending machine may include a translatable frame attached to any of the movable elements and the patient-specific implant.

The implant customization portion may include a cutting mechanism such that the implant blank may be cut to form the patient-specific implant. The implant customization portion may include a bending mechanism and a cutting mechanism such that the implant blank may be cut and bent to form the patient-specific implant.

Further in accordance with the first aspect, the implant customization information may include CT, X-ray, fluoroscopy or other visualization data of a target body location receiving the implant. The CT, X-ray, fluoroscopy or other visualization data may be obtained by a visualization system located within the sterile environment. The implant customization information may further include stored database information of target body location.

Still further in accordance with the first aspect, the interface may allow input from an operator to modify the customization information. The apparatus may further include a display device to display a virtual patient-specific implant generated by the customization information.

The patient-specific implant may be a bone plate and the customization information may include virtual bone reduction information to generate a patient-specific bone plate. The customization information may include shape and dimensional information of the patient-specific implant. The customization information may be derived from a flexible template positioned on the target body location.

A second aspect of the present invention is a method for implant customization in a surgical care environment. A method in accordance this aspect of the invention may include the steps of obtaining information related to a target body region to receive an implant, selecting an implant blank based on this information, and customizing the implant blank within the surgical care environment. The implant blank may be customized with a customization apparatus to manipulate the implant blank to a patient-specific implant based on the information. The customization apparatus may be located in a surgical care environment such that the customization may be performed intraoperatively or preoperatively.

In accordance with the second aspect, the customization apparatus may include a bending mechanism. The step of customizing the implant blank may be performed by bending the implant blank with the bending mechanism to generate the patient-specific implant based on the information. The customization apparatus may include a cutting mechanism. The step of customizing the implant blank may be performed by cutting the implant blank with the cutting mechanism to generate the patient-specific implant based on the information. The customization apparatus may include a bending mechanism and a cutting mechanism. The step of customizing the implant blank may be performed by bending and cutting the implant blank by the bending mechanism and the cutting mechanism respectively to generate the patient-specific implant based on the information.

Further in accordance with the second aspect, the step of obtaining the information may be performed by CT, X-ray, fluoroscopy or other visualization means of the target body location.

Sill further in accordance with the second aspect, the step of obtaining the information may include the steps of placing a flexible template on the target body location, manipulating the flexible template based on the target body location, and communicating shape and dimensional information of the manipulated flexible template to the customization apparatus. The flexible template may be manipulated to correspond to the patient specific implant.

The target body location may be a fractured bone and the information may include information related to a virtual bone reduction of the fractured bone. The patient-specific implant may be a patent-specific bone plate that corresponds to the virtual bone reduction information. The step of selecting an implant blank may be performed by evaluating the information to minimize customization of the selected implant blank to generate the patient-specific implant. The step of customization may be performed intraoperatively such that the implant blank may be manipulated to the patient-specific implant in under 60 minutes. The customization apparatus may be maintained under sterile conditions such that the patient-specific implant generated from the customization apparatus is sterile.

Still further in accordance with the second aspect, the method may further include the step of receiving the patient-specific implant from the customizing apparatus located in the surgical environment, and implanting the patient-specific on the target body location.

In a third aspect of the present invention, a surgical system for generating patient-specific implants is provided. A surgical system according to this aspect may include a flexible template, a data collection element and a customization apparatus. The flexible template may be manipulated on a target body region to correspond to a patient-specific implant. The data collection element may gather and communicate information related to the manipulated flexible template. The customization apparatus may include a storage portion having one or more implant blanks, an implant customization portion, and an interface configured to communicate with the data collection element. The information may be used by the customization portion to intraoperatively or preoperatively manipulate the implant blank to a patient-specific implant in a surgical care environment.

In a fourth aspect of the present invention, an apparatus for customizing an implant is provided. The apparatus may include a receiving portion for receiving one or more implant blanks, an implant customization portion for customizing the implant blanks and an interface configured to receive implant customization information. The apparatus may be located in a sterile environment such that the implant customization information may be used by the customization portion to intraoperatively manipulate the implant blank to a patient-specific implant within the sterile environment.

In accordance with this aspect, the receiving portion and the implant customization portion may be sterile such that the implant blanks remain sterile during and after customization. The apparatus may include a storage portion to store implant blanks received by the receiving portion. The storage portion may be configured to store the implant blanks under sterile conditions.

In accordance to a fifth aspect of the present invention, a surgical method to perform a surgical procedure is provided. The surgical method may include the steps of transmitting patient data to a surgical planning system, performing a virtual surgical planning based on the patient data, transmitting the virtual surgical planning to a hub, fabricating a surgical kit at the hub based on the virtual surgical planning, and delivering the surgical kit to an operating environment in a sterile condition. The surgical kit may include implants, surgical tools and other accessories to perform a surgical procedure.

BRIEF DESCRIPTION OF THE DRAWINGS

A more complete appreciation of the subject matter of the present invention and the various advantages thereof can be realized by reference to the following detailed description, in which reference is made to the following accompanying drawings:

FIGS. 14A-I are schematic views showing various stages of a preoperative diagnostic support for virtual surgical planning of the surgical procedure work flow shown in FIG. 12;

FIGS. 27A and 27B are schematic views of implant bending machine according to still yet another embodiment of the present invention.

DETAILED DESCRIPTION

Figure 1:
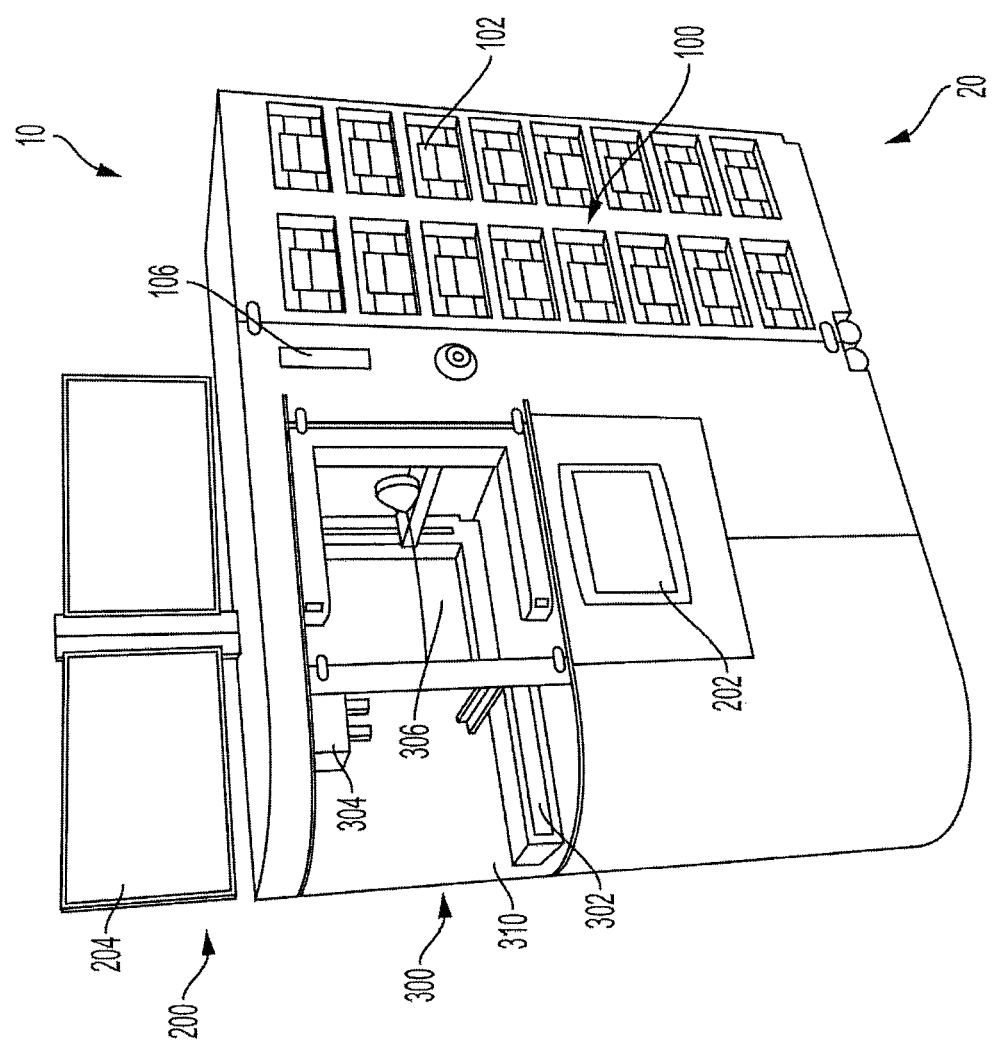
FIG. 1 is a perspective view of a customization device according to a first embodiment of the present invention.

FIG. 1 illustrates a customization device 10 according to an embodiment of the present invention. Customization device 10 includes various components such as a storage portion 100, an interface 200 and a customization portion 300. While the various components are assembled to form an integrated customization device 10 in FIG. 1, other embodiments may have modular components configured to be located apart from one another. For example, interface 200 can be located away from storage portion 100 and customization portion 300 for a customization device 10 configured to allow an operator to remotely control and monitor the customization device.

Figure 2:
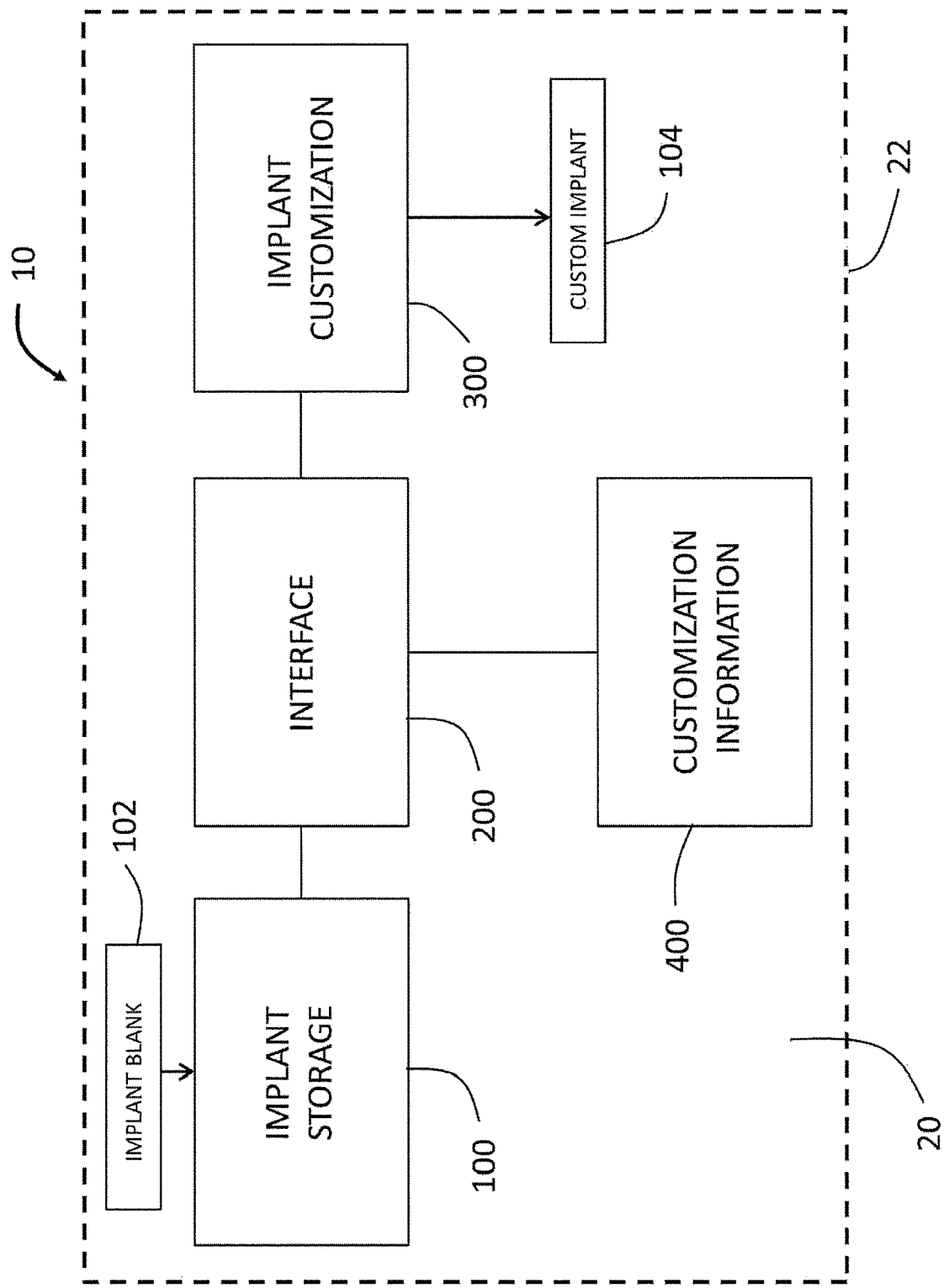
FIG. 2 is a schematic drawing of the customization device of FIG. 1.

Referring now to FIG. 2, there is shown a schematic drawing of customization device 10. Customization device 10 is located in a sterile environment 20 such as an operating room or other surgical setting defined by a sterile boundary 22. While all components of customization device 10 are located within sterile boundary 22 in this embodiment, other embodiments can have some components located outside sterile boundary 22. Interface 200 is configured to receive customization information 400 and utilize this information to customize implants. For example, an implant blank 102 stored in storage portion 100 can be customized in customization portion 300 to produce a custom implant 104 based on customization information 400 processed by interface 200. Customization device 10 is fully sterilized and configured to be placed and operated within sterile environment 20. Hence, the sterility of the implant and sterile environment 20 is maintained throughout the customization process. Accordingly, an operator can determine patient-specific implant requirements, virtually customize the implant using interface 200, and fabricate a patient-specific custom implant 104 within the confines of sterile environment 20. Thus, as more fully explained below, custom implants can be created on-demand intraoperatively by utilizing customization device 10.

Figure 3:
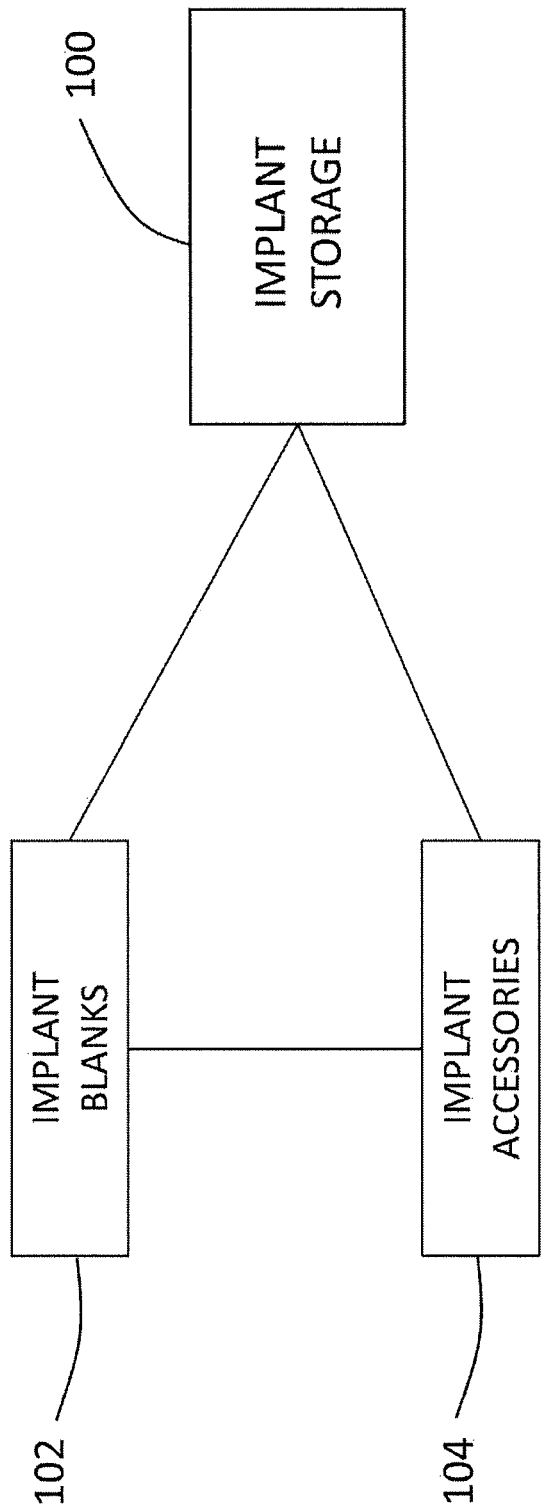
FIG. 3 is a schematic drawing of a storage portion of the customization device of FIG. 1.

While FIG. 1 illustrates one embodiment of customization device 10, FIGS. 2-6 show schematic drawings of the various components of that device. As best shown in FIGS. 1 and 3, storage portion 100 includes implant blanks 102 and implant accessories 106. Implant blanks are provided in various dimensions and shapes that can be customized to cover the needs of a diverse patient population. As more fully explained below, customization portion 300 allows for a wide range of implant customization and consequently reduces the implant blank inventory requirement. Examples of implant blanks stored in storage portion 100 can include bone plates, rods, cups, dental implants, etc. Implant accessories 106 can include bone fasteners, nails, targeting devices, etc., associated with the implant blanks. Sterilized implant blanks 102 and sterilized implant accessories 106 can be preloaded into the sterilized storage portion. Storage portion 100 can include a sterilization unit that allows for sterilization of unsterilized implant blanks and implant accessories.

Figure 4:
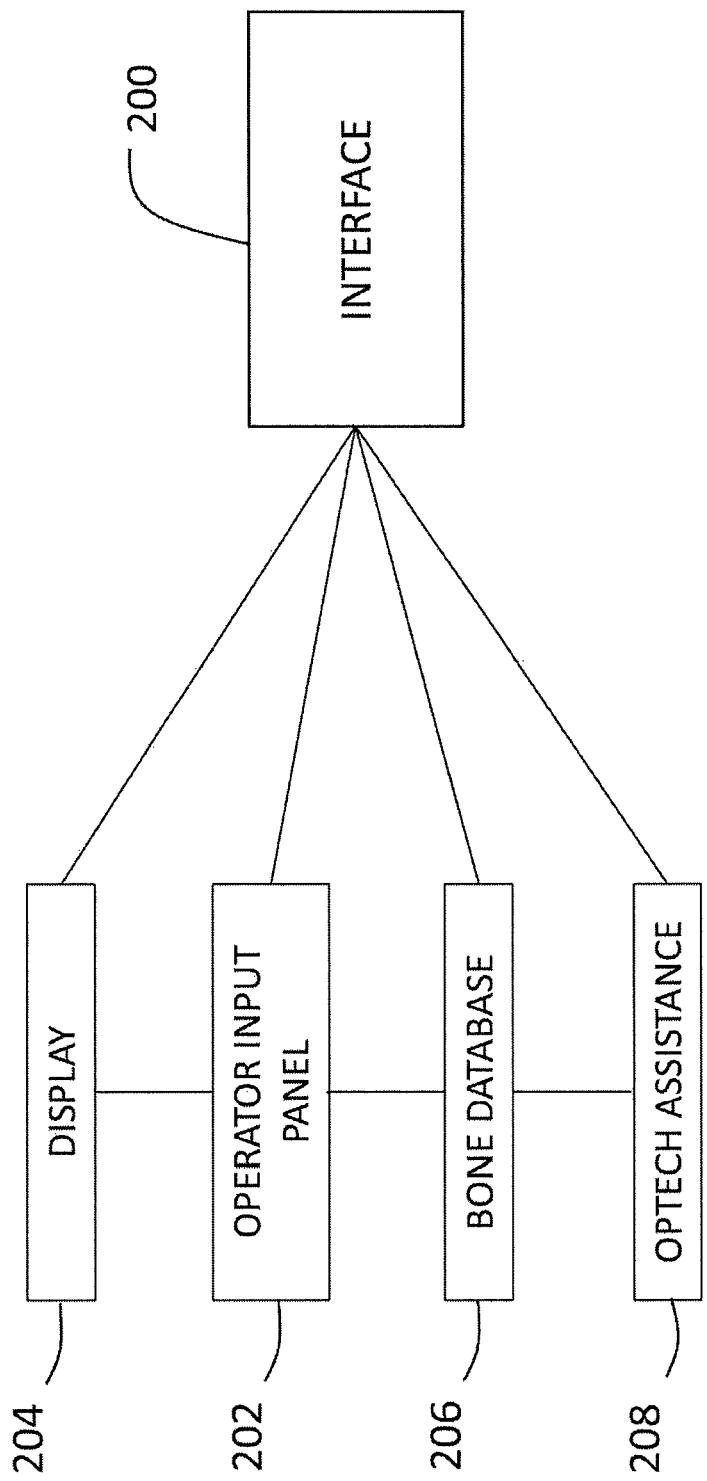
FIG. 4 is a schematic drawing of an interface of the customization device of FIG. 1.

Interface 200 includes a display 204 and an operator input panel 202 as best shown in FIG. 4. Operator input panel 202 allows an operator to control and monitor the customization device 10. For example, an operator can input patient-specific information for implant customization, manually select an implant blank size, access a bone database 206 or operational technical assistance through interface 200. Interface 200 is configured to access implant customization information 400 as more fully discussed below. An operator can evaluate virtual implant design via interface 200 and make adjustments to customize the virtual implant design as necessary. Interface 200 can also select implant-related accessories such as fasteners from implant accessories 106 to match the precise requirements of the customized implant. All of this information can be conveyed to the operator via display 204.

Figure 5:
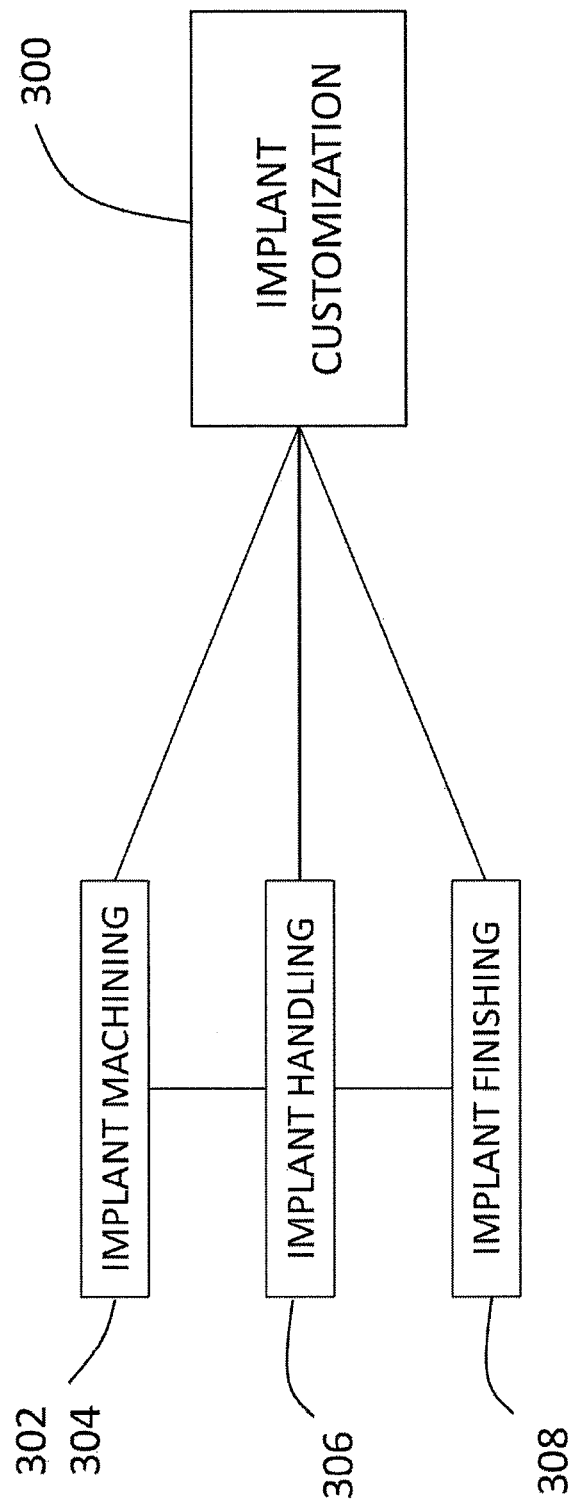
FIG. 5 is a schematic drawing of a customization portion of the customization device of FIG. 1.

Customization portion 300 includes an implant machining section, an implant handling section 306, and an implant finishing section 308 as shown in FIG. 5. The implant machining section can include machining mechanisms such as a cutting mechanism 302 and/or a bending mechanism 304 as shown in FIG. 1. Various other machining mechanisms such as drilling, reaming, grinders, etc., can be incorporated into customization portion 300 based on the implant type and customization requirements. Machining mechanisms such as cutting mechanism 302 and bending mechanism 304 are specifically designed to operate within the sterile environment of customization device 10. Cutting mechanism 302 can include a laser beam cutting mechanism or a mechanical shear cutting mechanism. The laser beam cutting mechanism can include protective gases within customization portion 300 to prevent flaming and other hazardous conditions that may occur during laser beam cutting operations. Mechanical shear cutting mechanism can be carried out by electromechanical or hydraulic forces that can shear implant blanks. Mechanical shear cutting can be combined with grinding means to remove burrs and other imperfections that may arise from mechanical shear cutting. Bending mechanism 304 can shape implant with three degrees of freedom and can include two bending and a torsion means configured for biomechanical bending of implants.

Figure 24:
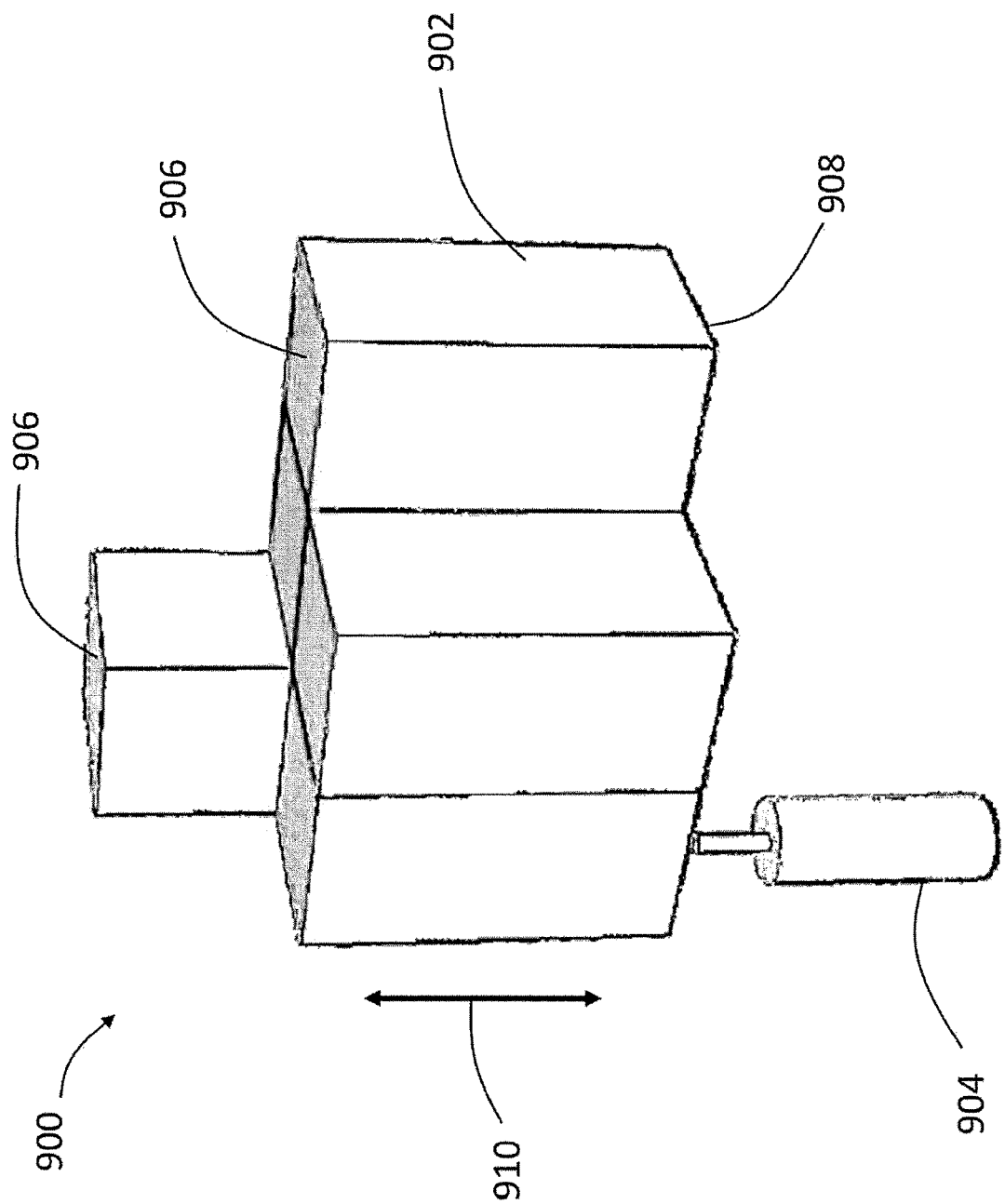
FIG. 24 is a perspective view of an implant bending machine according to an embodiment of the present invention.

FIG. 24 shows an example of an implant bending mechanism 900 according to an embodiment of the present disclosure. Implant bending mechanism 900 includes several movable elements 902 arranged in an array with each element having an implant contacting surface 906 and an opposite surface 908. Each of these movable elements 902 can be individually moved along direction arrow 910 by an actuator 904. Actuator 904 can include any actuating mechanism such as a stepper motor (shown in FIG. 24) to translate the movable elements 902. Each movable element 902 can include an independent actuator 904 to translate each element such that the contacting surfaces of elements 902 assume the profile of the desired custom implant. Interface 200 controls translation of elements 902 by actuators 904 based on the shape of implant blank 102 and the shape of the desired custom implant. Once the movable elements 902 assume the profile of the desired custom implant, implant bending machine 900 is pressed against implant blank 102 to generate the custom implant 104. In other embodiments, each movable element can be individually moved to shape the implant blank. While a single actuator is shown in FIG. 24, implant bending mechanisms in other embodiments may have multiple actuators including separate actuators for each movable element 902. While the movable elements 902 are shown as cuboid-shaped structures adjoining each other in this embodiment, other embodiments may have differently shaped structures such as cylindrical-shaped structures, spherically-shaped structures, etc., which may be spaced apart from each other.

Figure 25:
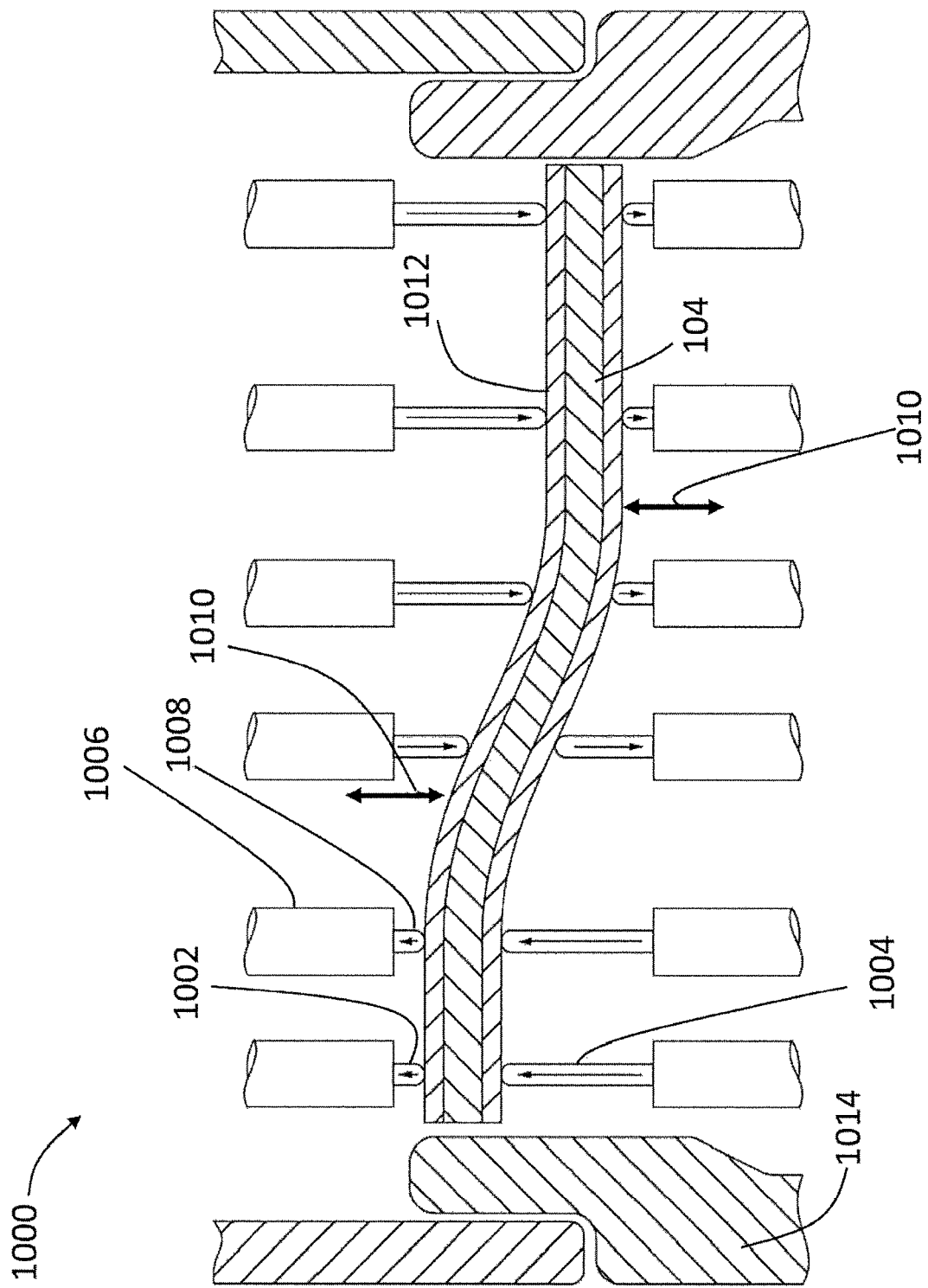
FIG. 25 is a schematic view of an implant bending machine according to another embodiment of the present invention.

Referring now to FIG. 25, there is shown an implant bending machine 1000 according to another embodiment of the present invention. Implant bending machine 1000 includes an upper row of movable elements 1002 and a lower row of movable elements 1004. Each movable element 1002, 1004 is connected to an actuator 1002 which translates the movable element 1002, 1004 along direction arrow 1010. A distal end 1008 of each movable element 1002, 1004 contacts implant blank 102 (a plate is shown as an example of an implant blank in FIG. 25) to bend the implant blank to the desired custom implant 104. An adjustable frame 1014 is used to firmly secure the implant blank 102 to facilitate bending by the implant bending machine. Interface 200 controls translation of elements 1002, 1004 by actuators 1006 based on the shape of implant blank 102 and the shape of the desired custom implant 104. Once the movable elements 1002, 1004 assume the profile of the desired custom implant, implant bending machine 1004 forces the two rows of movable elements against implant blank 102 to generate the custom implant 104. A cover layer 104 may be used to protect the implant blank 102 from damage during bending as shown in FIG. 25. While each of upper row movable elements 1002 is aligned with their respective lower row movable elements 1004 in this embodiment, other embodiments may have the upper row and low row movable elements offset to each other.

Figure 26:
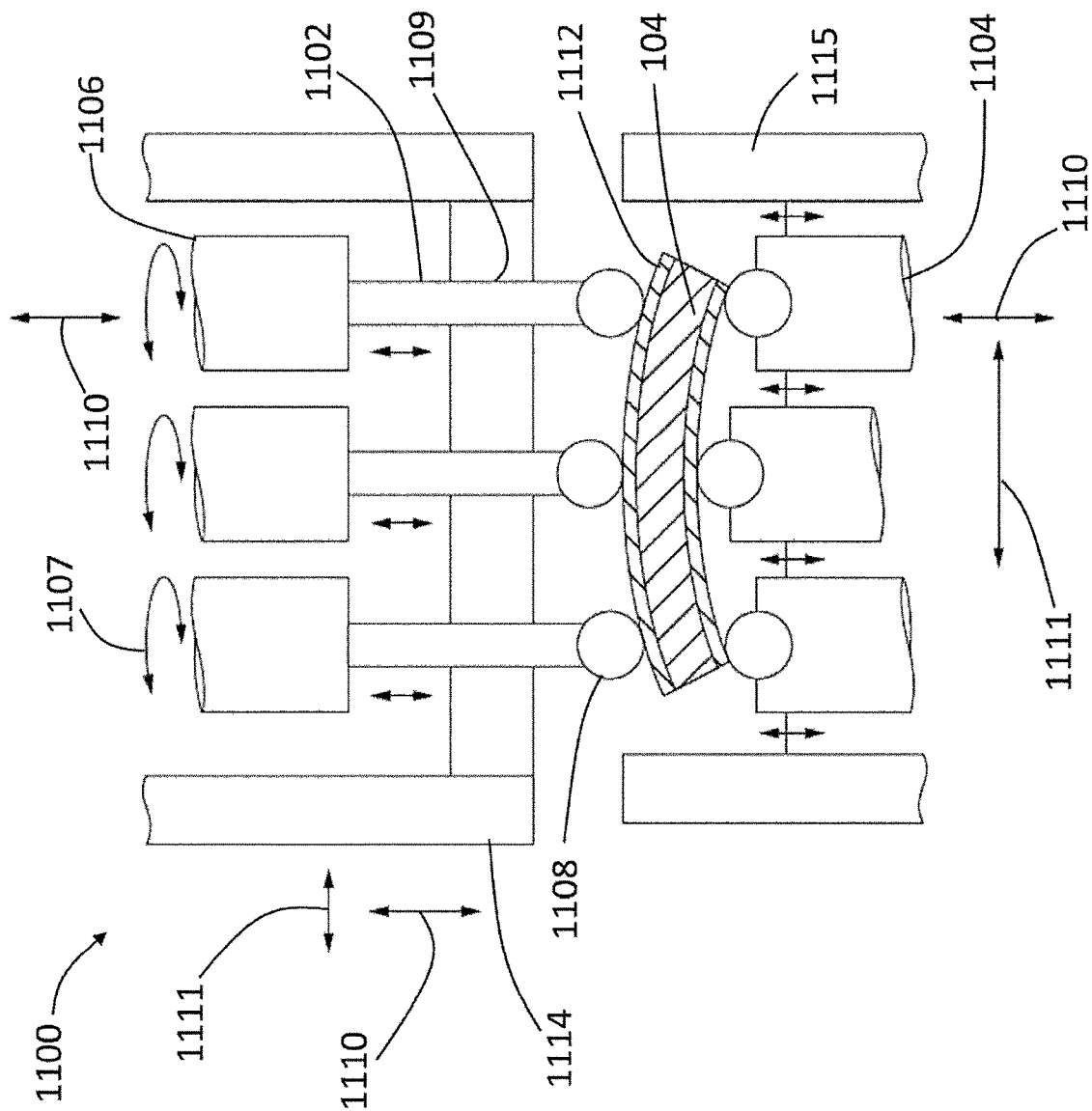
FIG. 26 is a schematic view of an implant bending machine according to yet another embodiment of the present invention.

FIG. 26 shows an implant bending machine 1100 according to another embodiment of the present invention. Implant bending machine 1100 is similar to implant bending machine 1000, and therefore like elements are referred to with similar numerals within the 1100-series of numbers. For instance, implant bending machine 1100 includes upper movable elements 1102 and lower movable elements 1104 which are translated by actuators 1106. However, movable elements 1102, 1104 include externally threaded portions 1109 which engage with internal threads of upper frame 1114 and lower frame 1110 respectively to translate implant contacting surface 1108 along direction 1110. The threaded linear translation of movable elements 1102, 1104 allows for precise linear translation. Actuators 1106 impart a twisting force as shown by direction arrow 1107 to translate the movable elements along direction 1110. Implant contacting surface 1108 is shaped as a spherical point in this embodiment to prevent damage to custom implant 104 during bending. Upper frame 1114 and lower frame 1115 of implant bending machine 1100 are also movable along direction 1111 and direction 1110 as shown in FIG. 26. Interface 200 can control individual movement of upper frame 1114 and lower frame 1115 during the bending process.

FIGS. 27A and 27B show an implant bending machine 1200 according to another embodiment of the present invention. Implant bending machine 1200 is similar to implant bending machine 1100, and therefore like elements are referred to with similar numerals within the 1200-series of numbers. For instance, implant bending machine 1200 includes upper movable elements 1202 and lower movable elements 1204 which are translated by actuators 1206. However, movable elements 1202, 1204 have rollers 1208 to bend implant blank 102 in this embodiment. Each movable element can be individually moved along direction 1210 by actuators 1206 which are controlled by interface 200. Implant blank 102 and/or the frames 1214, 1215 can be moved relative to each other along direction 1211 to create custom implant 104. FIGS. 27A and 27B show rollers 1208 of implant bending machine 1200 in first and second configurations to customized bending of implant blank 102. While the implant bending machine embodiments discussed here are controlled by interface 200, these implant bending machines can be manually controlled by an operator in other embodiments.

Implant handling 306 may provide handling means with five degrees of freedom to move and position the implant within customization portion 300 during machining. Implant handling 306 can select a suitable implant blank 102 from storage portion 100 and move the implant blank to the customization portion 300. As described above, implant blank selection can be manually performed by an operator via interface 200 or customization device 10 can automatically select an implant blank 102 base on predetermined criteria. Implant blank 102 selection can be based on, inter alia, minimizing the machining requirement to customize the implant. For example, if a patient requires an implant with a specific shape, interface 200 will select an implant blank that is most similar to the required size and shape in order to minimize the bending operations to customize the implant.

Implant finishing 308 can include means to clean and resterilize the finished implant after machining if necessary. Sterilization means can include ethylene oxide (ETO), hydrogen peroxide, autoclaving, dry heating or other means. A viewing portal 310 on customization portion allows an operator to visually monitor customization.

Figure 6:
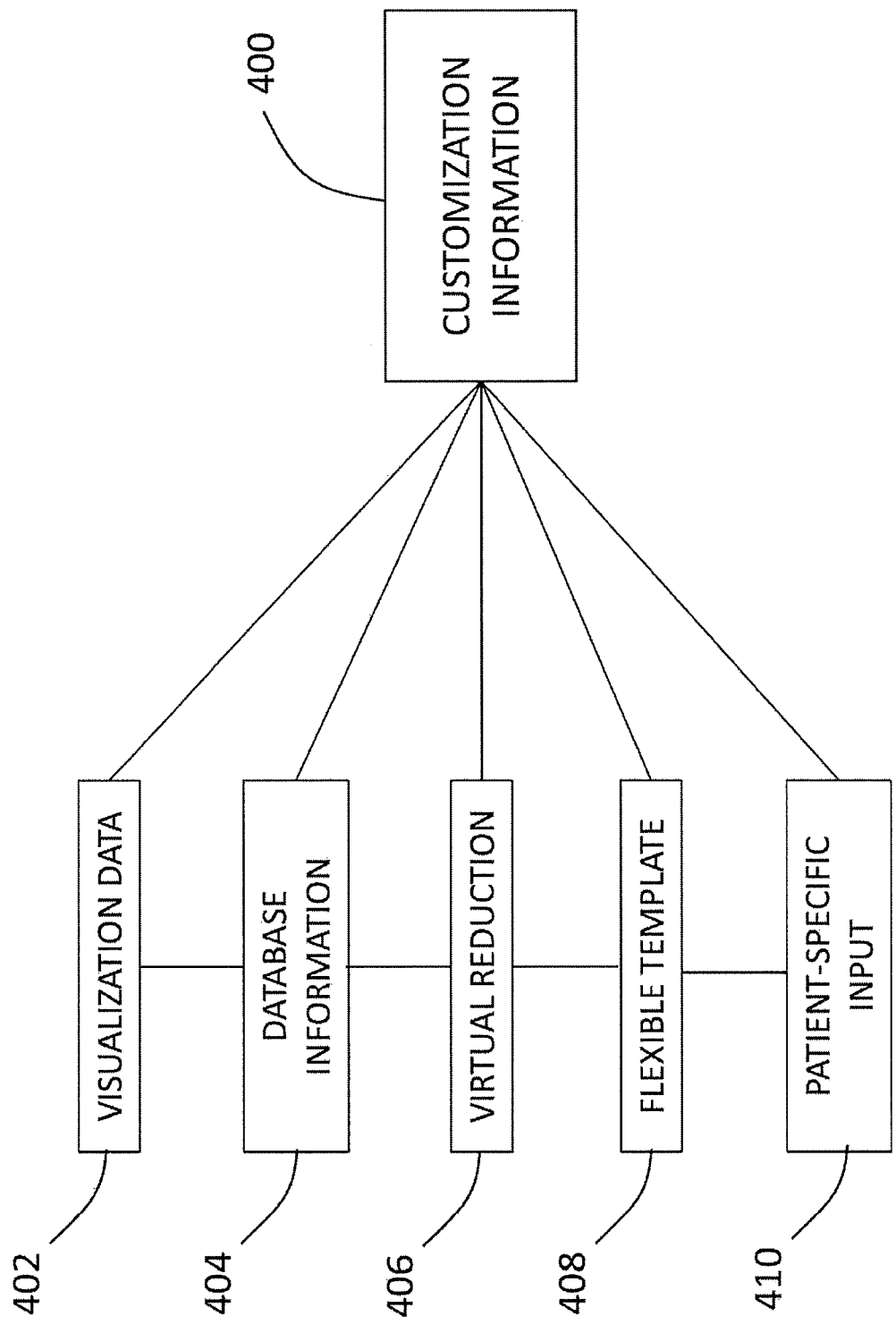
FIG. 6 is a schematic drawing of customization information utilized by the customization device of FIG. 1.

Customization information 400 available to interface 200 can include many different kinds of data as shown in FIG. 6. Visualization data 402 of the target body location can be obtained from any visualization means such as X-rays, CT scans, fluoroscopy, ultrasound scans, electrical impedance imaging, etc. For example, a bone plate to treat a bone fracture will require visualization data 402 of the fractured bone and also a contralateral healthy bone for bone plate customization. Equipment to obtain visualization data can be located within sterile environment 20 to allow for pre-operative or intraoperative collection of visualization data or the necessary scans can be obtained outside of that environment and uploaded to device 10.

Database information 404 containing bone data obtained from a population sample can be utilized to customize implant for patient-specific needs. For example, a fractured bone can be compared with similar healthy bone samples from the bone database to precisely size a bone plate to treat the fracture. Similarly, virtual bone reduction data 404 can be obtained from the database to perform a virtual bone reduction of the fractured bone prior to sizing a patient-specific implant. As more fully explained below, a flexible template 40 can be placed on the target body location and manually contoured to match the target bone shape. The contoured template can then be used to generate a custom implant.

Patient-specific data 410 can also be directly input to interface 200 by an operator for implant customization. An operator can input patient-specific data 40 regarding gender, age, etc., as part of customization information 400 analyzed by interface 200 to customize the implant.

Customization device 10 can be fully automated wherein customization information 400 is automatically received by and processed in interface 200, the interface then automatically selects an appropriate implant blank 102 and implant accessories 106, and customizes implant blank 102 in customization portion 300 to produce custom implant 104. Other embodiments of customization device 10 can have semi-automated components allowing an operator to manually operate and control different stages of customization device 10. For example, an operator can manually control and make adjustments to the virtual design of the custom implant on interface 200. The automation level of custom device 10 can be configured based on where the customization device is to be located and the type of implant customization required. For example, a customization device designed to be located in an operating room can be fully automatic, whereas a customization device intended to be located in other areas of a hospital can be semi-automatic. Custom implant 104 can be pre-operatively prepared or intraoperatively prepared within sterile environment 20.

Figure 7B:
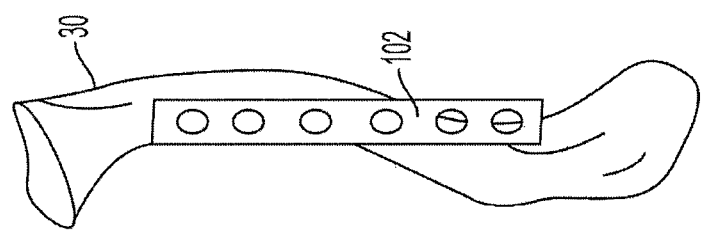
FIG. 7B shows a front view of a patient-specific implant disposed in relation to the bone customized from the implant blank of FIG. 7A utilizing the customization device of FIG. 1.
Figure 7A:
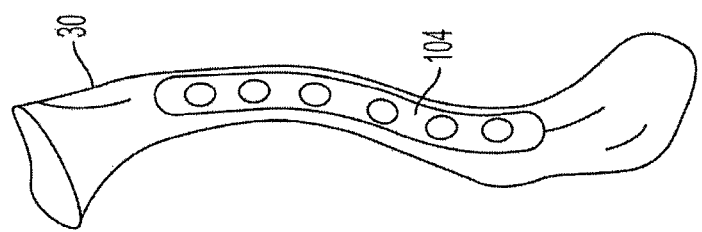
FIG. 7A shows a front view of an implant blank disposed in relation to a bone.

Referring now to FIGS. 7A and 7B, there is shown an example of implant blank 102 and custom implant 104 respectively, projected on a visualization of a target bone 30. Visualization of target bone 30 can be obtained by any of the methods described above. As best shown in FIG. 7A, implant blank 102 does not match the shape and length requirement of bone 30. Customization device 10 is used to customize implant blank 102 to produce custom implant 104. Custom implant 104 matches the shape and length of target bone 30 has best shown in FIG. 7B.

Figure 8:
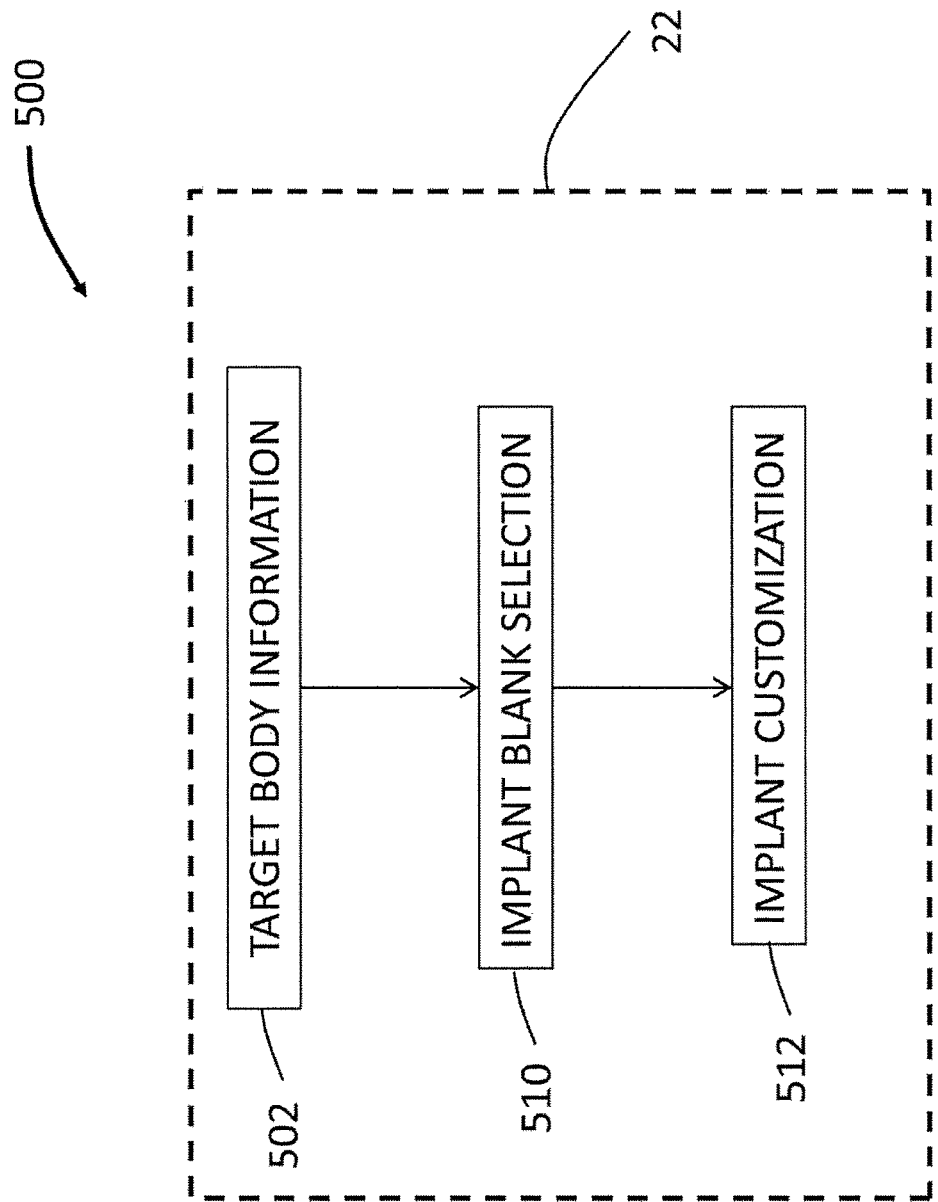
FIG. 8 is a flowchart showing the steps for performing an implant customization according to another embodiment of the present invention.

A method for implant customization 500 utilizing customization device 10 according to another aspect of the present invention is shown in FIG. 8. In step 502, target body information of a recipient bone is collected. The target body information can include X-rays, ultrasound scans, fluoroscopy, etc., collected by any of the visualization means described above. Target body information 502 is then transmitted to interface 200 of customization device 10. Customization device 10 can then be used to select an implant blank 102 from storage portion 100 in step 510. Implant blank 102 selection is based on customization information 400 as more fully explained above. Suitable implant accessories 106 to match implant blank selection can be selected from storage portion 100. Customization device 10 performs implant customization in step 512 to customize selected implant blank 102 to custom implant 104.

Figure 9:
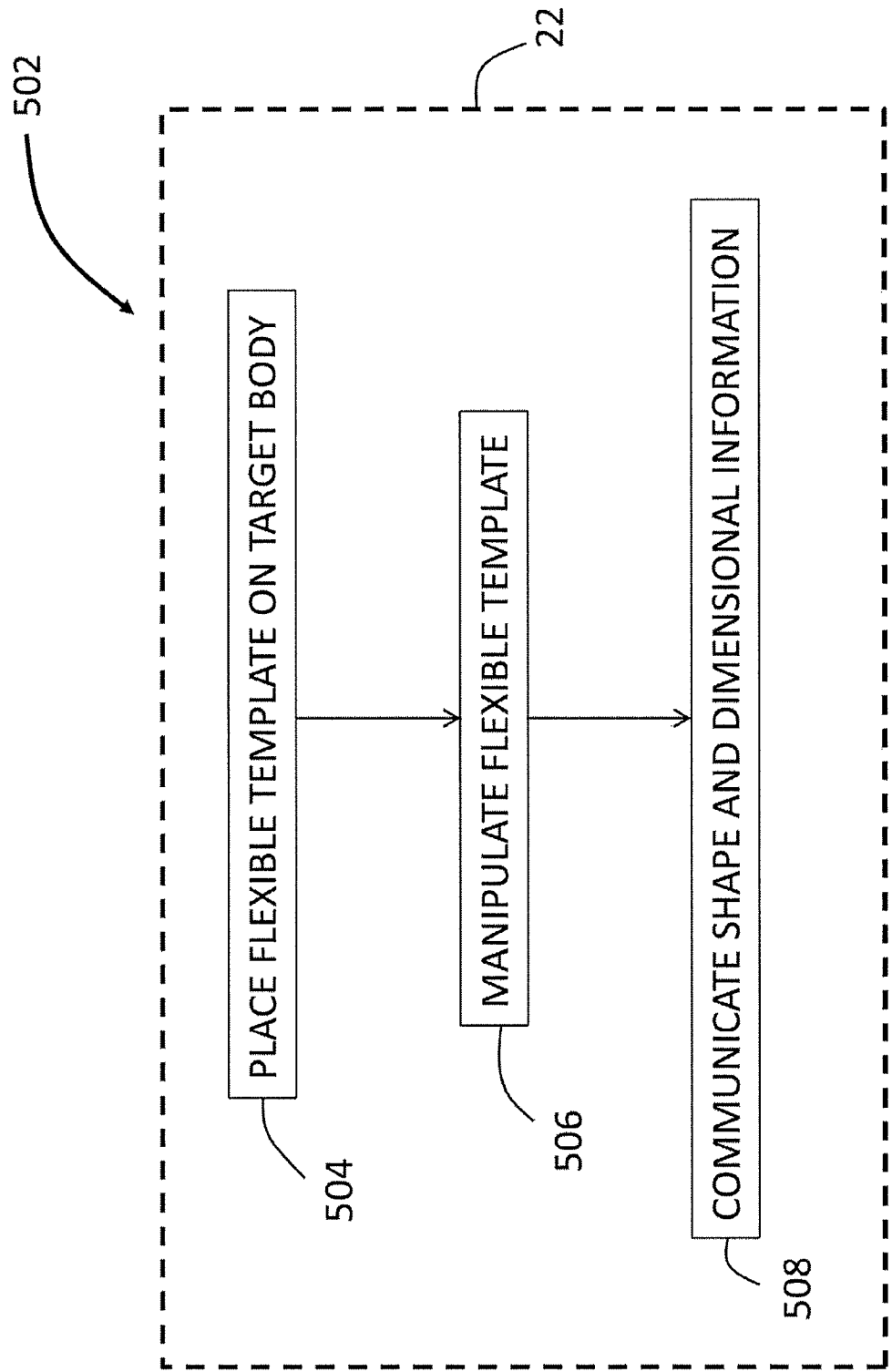
FIG. 9 is a flowchart showing the steps to utilize a flexible template for implant customization according to another embodiment of the present invention.
Figure 10C:
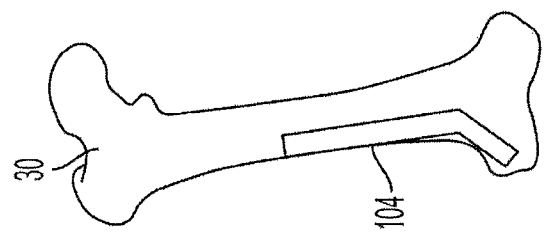
FIGS. 10A-10C are front views of a bone fracture, a flexible template and a customized implant respectively showing the sequential steps of utilizing the flexible template for implant customization.
Figure 10B:
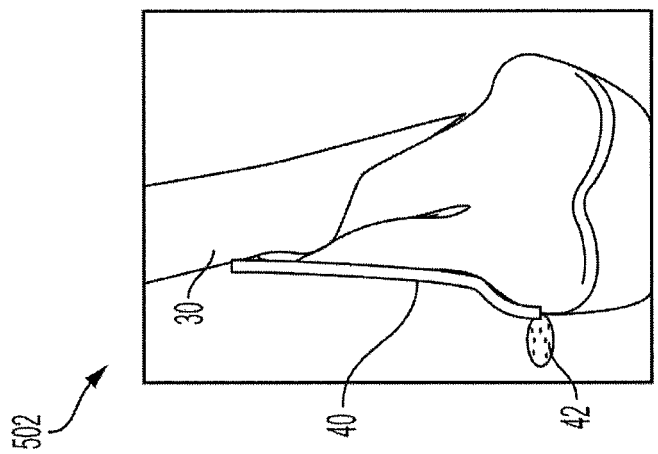
Figure 10A:
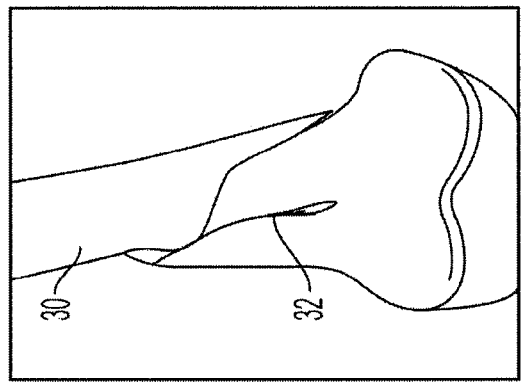

Referring now to FIGS. 9 through 10C, there is shown a method for obtaining target body information 502 using flexible template 40 according to another embodiment of the present invention. A custom implant to treat a bone fracture 32 on bone 30 as shown in FIG. 10A is described in method 502. Flexible template 40 is placed on bone 30 in step 504. Flexible bone template 40 may be generally similar in size to the required custom implant and made of a flexible, pliant material. Flexile template 40 includes a marker 42 which can be captured on an X-ray as best shown in FIG. 10B. In step 506, an operator can manually contour flexible template 40 to match the shape of the target area on bone 30 and to cover fracture 32. Once flexible template 40 acquires the desired shape, this information can be sent to customization device 10 to select an implant blank and customize the blank to match flexible template 40. As shown in FIG. 10C, custom implant 104, which is a precise match to flexible template 40, is fabricated by customization device 10.

Figure 11:
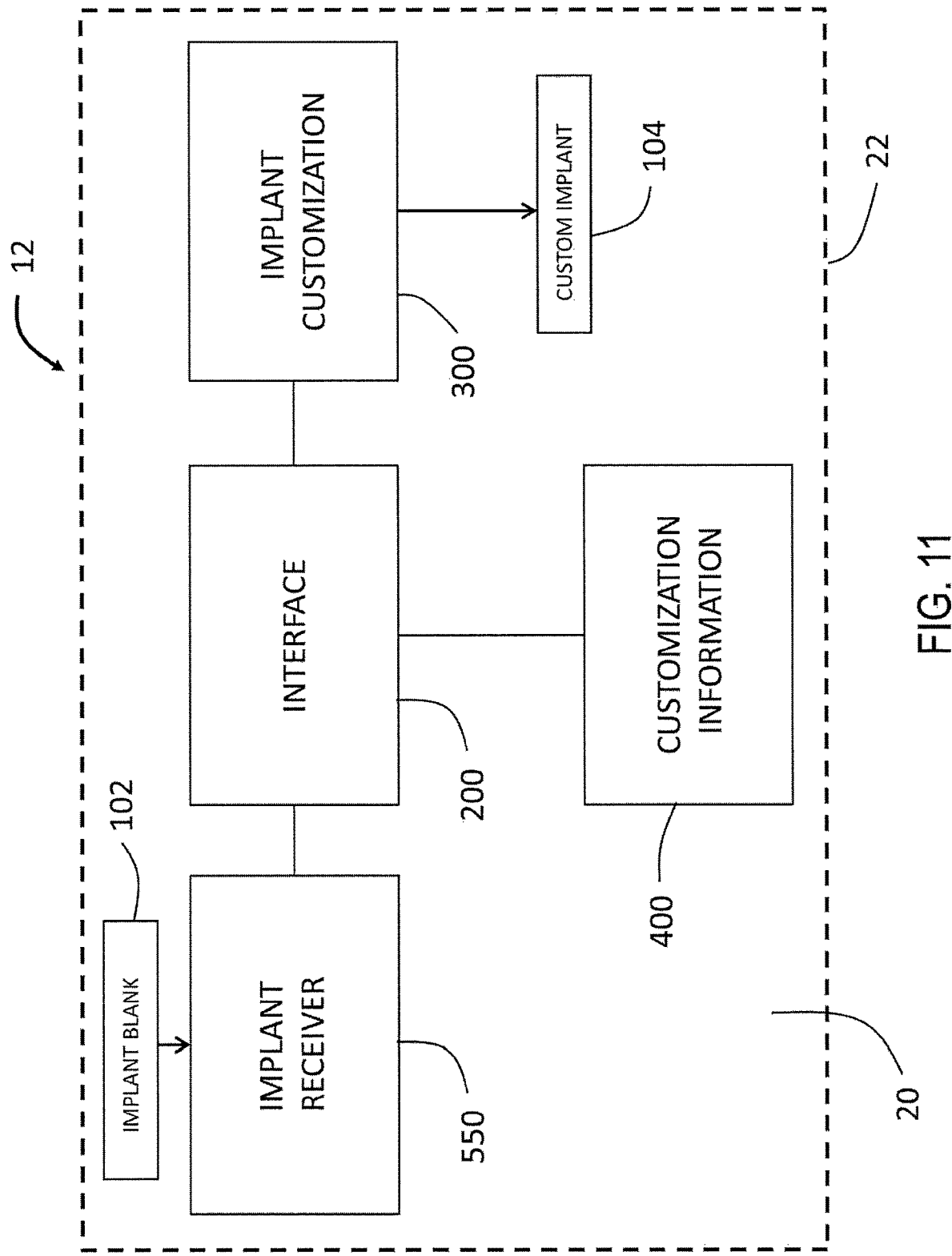
FIG. 11 is a schematic drawing of a customization device according to another embodiment.

FIG. 11 is a schematic drawing of a customization device 12 according to another embodiment of the present invention. Customization device 12 is similar to customization device 10, and therefore like elements are referred to with similar numerals. For instance, customization device 12 includes interface 200 and customization portion 300. However, customization device 12 has an implant receiver 550 instead of a storage portion 100. Implant receiver 550 is configured to receive and transport implant blank 102 to customization portion 300 while preserving the sterility of implant blank 102. Implant receiver 550 is suitably situated on customization device 12 to conveniently receive implant blank 102 from an operator or an automated delivery system (not shown). Customization device 12 will require less space within sterile environment 20 as no implant storage space is required. Customization device 12 may be provided with a storage portion to store implant blanks 102 in other embodiments.

Figure 12:
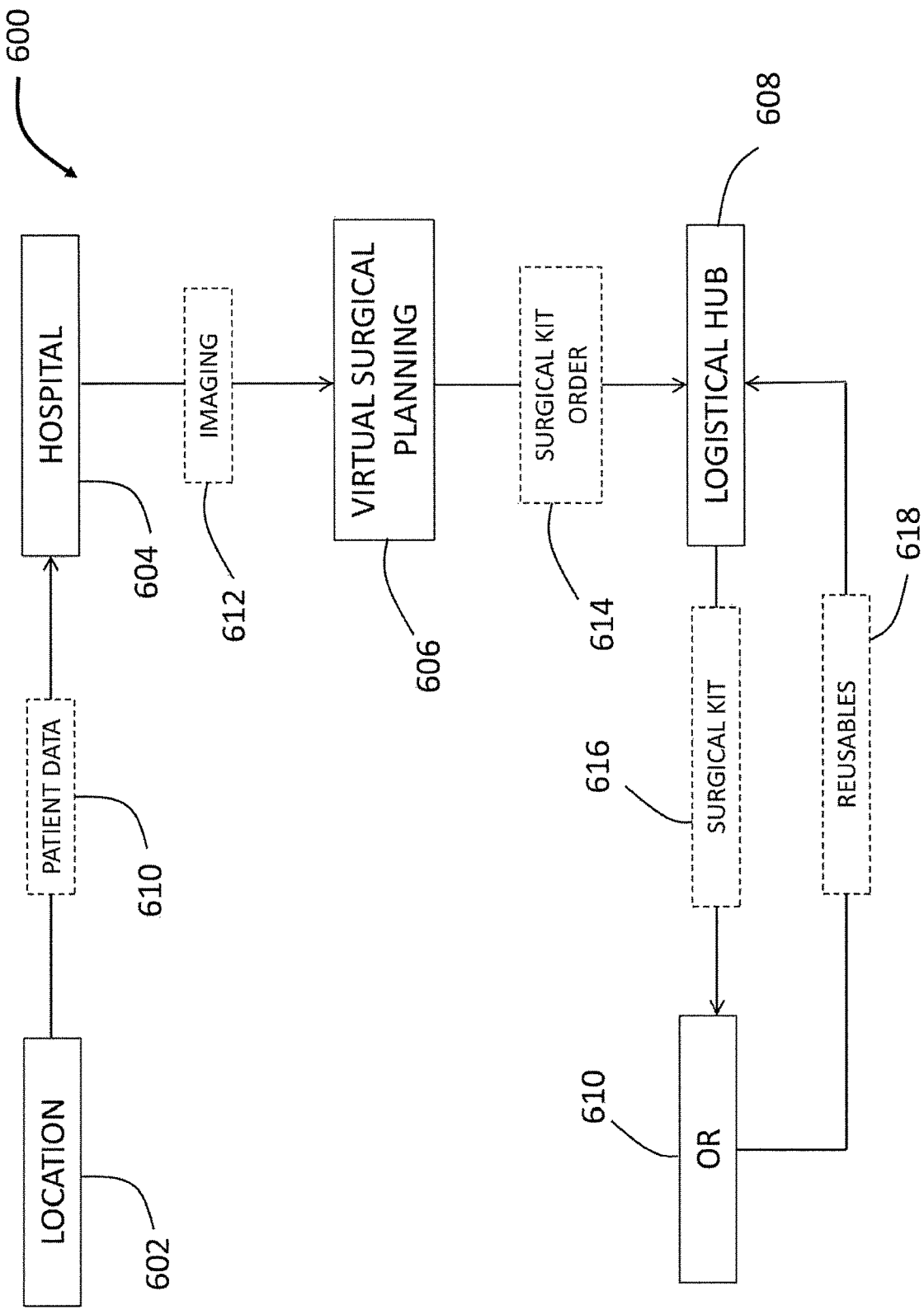
FIG. 12 is a schematic drawing of a surgical procedure work flow according to another embodiment of the present invention.

Referring now to FIG. 12, there is shown a surgical procedure work flow 600 according to one embodiment of the present invention. Surgical procedure work flow 600 provides a comprehensive work flow for treating a patient beginning with the collection of patient data 610 at an incident location 602 where the patient suffers an injury. Patient data 610 can include patient bibliographic information such as age, sex, etc., patient general health condition such as blood pressure, heart rate, etc., and specific injury description observed at location 602 and during transportation of the patient to a hospital 604. Patient data 610 is transmitted to hospital 604 to allow the hospital to prepare for receiving the patient. Upon arrival of the patient at hospital 604, imaging data 612 of the patient's injury is obtained and transmitted to a virtual surgical planning system 606. Virtual surgical planning system allows an operator located in hospital 600 or remotely to perform virtual surgical planning and generate a surgical kit order 614, as more fully described below. A logistical hub 608 configured to receive surgical kit order 614 and generate a surgical kit 616 in accordance with the same can be located at hospital 604 or in a remote location. Surgical kit 616 is delivered to an operating room 610 to perform surgical procedure on the patient. Any reusable items 618 can be transported back to logistical hub 608. It is to be understood that surgical procedure work flow 600 shown here and described below in the subsequent paragraphs may be used for any surgical procedure. The various stages and steps described in surgical work flow 600 can be utilized as a single system as described in this embodiment, or they may be used as modular systems to accomplish specific tasks during a surgical procedure work flow.

Figure 13:
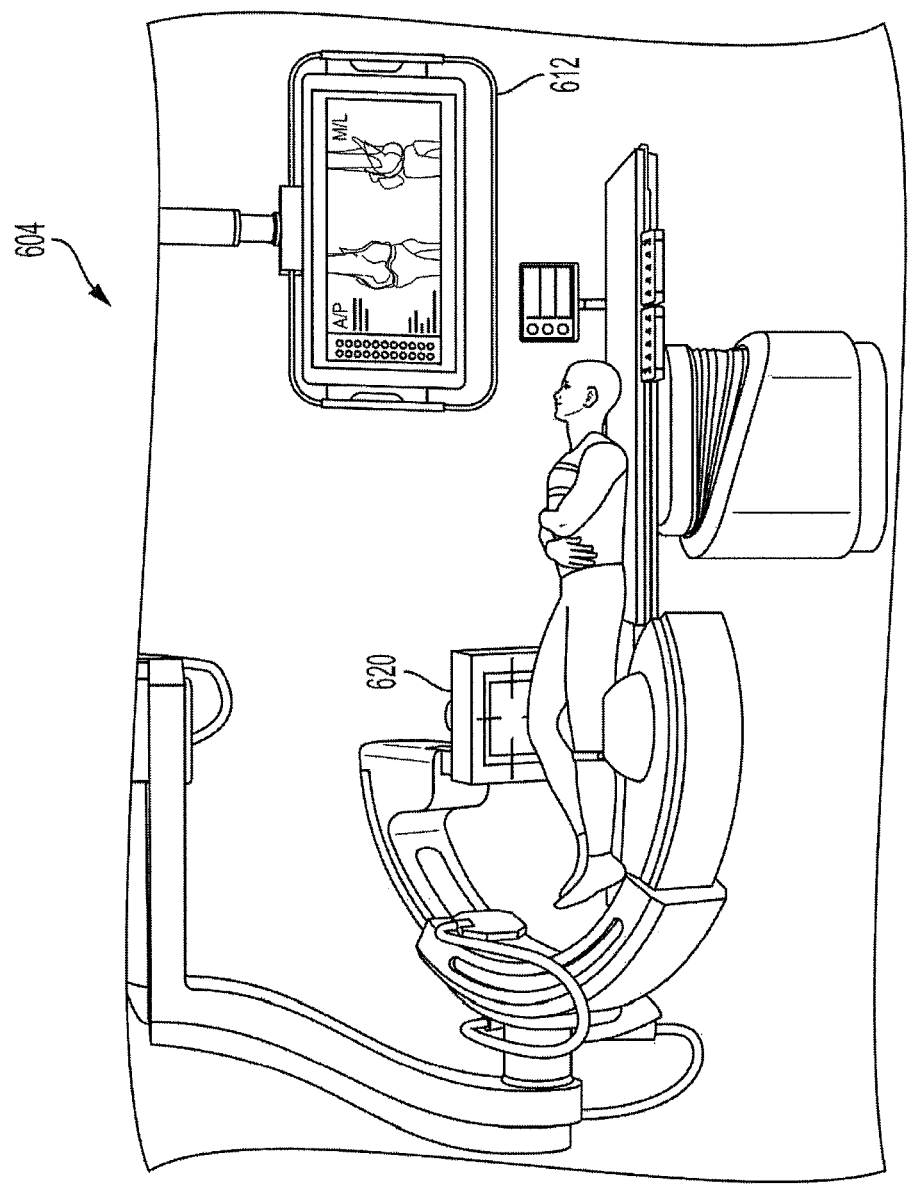
FIG. 13 is a perspective view of an imaging system of the surgical procedure work flow shown in FIG. 12.

FIG. 13 shows a perspective view of an imaging system 620 located in hospital 600. Imaging system 620 can include an X-ray device, as shown in FIG. 13, or any other imaging devices such as CT scanning, MRI scanning, etc. Imaging data 612 generated by imaging system 620 is transmitted to virtual surgical planning system 606. As shown in the present example, imaging data 612 includes X-ray image data of a distal femur fracture.

Figures 14C, 14D:
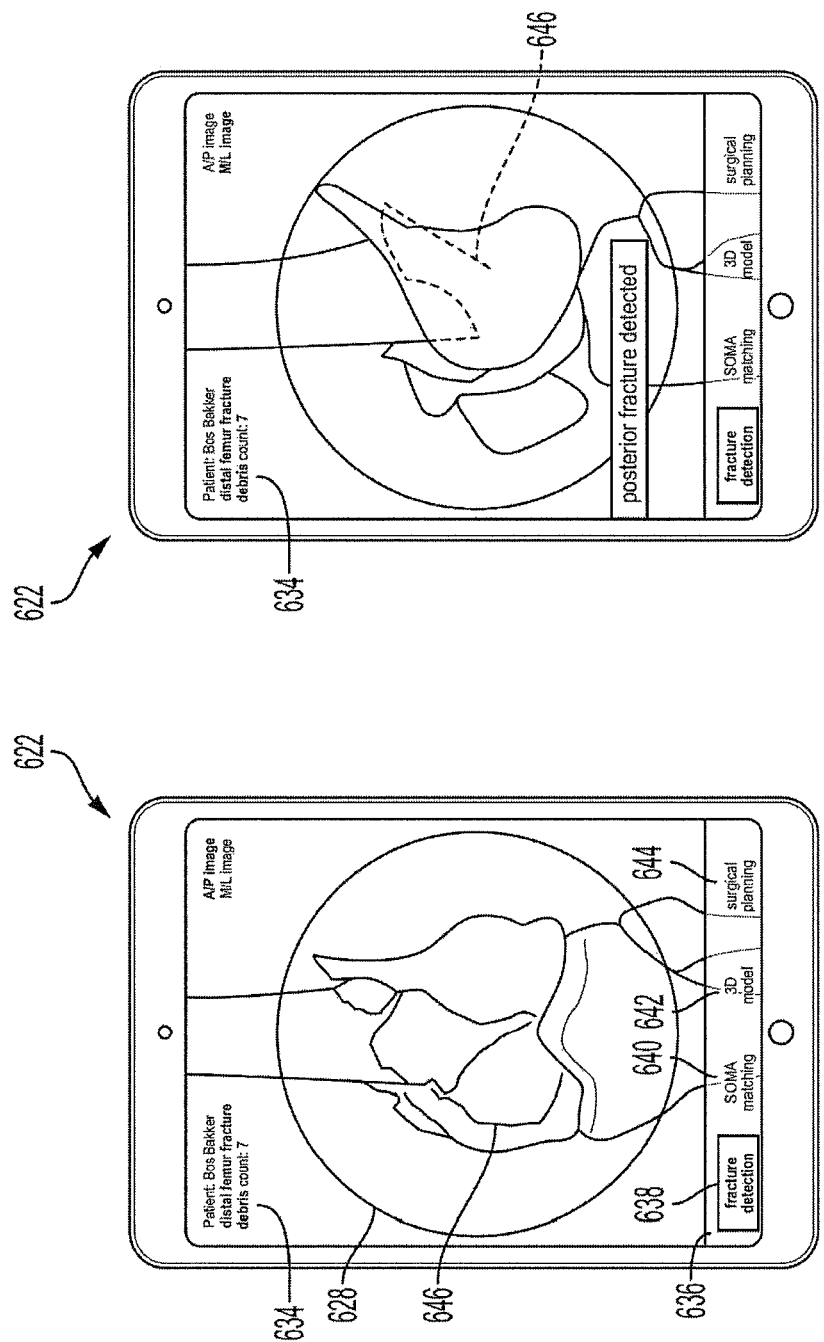

Referring now to FIGS. 14A-I, there is shown schematic views of various stages of virtual surgical planning system 606. Imaging data 612 and other associated patient data collected at location 602 and hospital 604 is transmitted to a display device. The display device can be a portable display device such as a tablet 624 (as depicted), a smart phone, or any other device such as desktop monitor coupled with a computer. Bone data 634 describing the specific patient injury, imaging data 612, description of the imaging data—i.e., x-ray image orientation, etc., are all displayed on tablet 624. An operator can move a cursor to focus on a zone of interest 628 by moving an image selection cursor 632 as best shown in FIG. 14B.

A fracture diagnostic support system 622 with a support menu 636 is shown in FIG. 14C. Support menu 636 includes routines for fracture detection 638, database matching 640, 3D modeling 642, and surgical planning 644. FIGS. 14C and 14D show fraction detection routine 638 on tablet 624, whereby diagnostic support system 622 identifies fracture lines 646 and fracture count 634. FIG. 14C depicts fracture lines 646 in anterior-posterior image and FIG. 14D depicts fracture lines 646 in a medial-lateral image.

Referring now to FIGS. 14E and 14D, there is show database matching routine 640 for the medial-lateral and anterior-posterior image respectively. Database matching routine 640 is performed by comparing the patient's image data 612 with a bone database including a plurality of bone samples. Bone samples may be obtained from X-ray, CT scan, MRI scan or other imaging means. Bone data along with bibliographic information can be collected, analyzed, and indexed for retrieval in the database. Bone data may include healthy, diseased or fractured bones, whether taken from the patient themselves or from other persons. Database matching routine 622 compares imaging data 612 with the database and generates a bone match outline 648 depicting an ideal representation of imaging data 612. As shown in FIG. 14F, in addition to the bone match outline 648, fracture diagnostic support system 622 generates a femoral axis 650, a tibial axis 652 and a dislocation distance 654 by comparing imaging data 612 with the database.

Figure 14I:
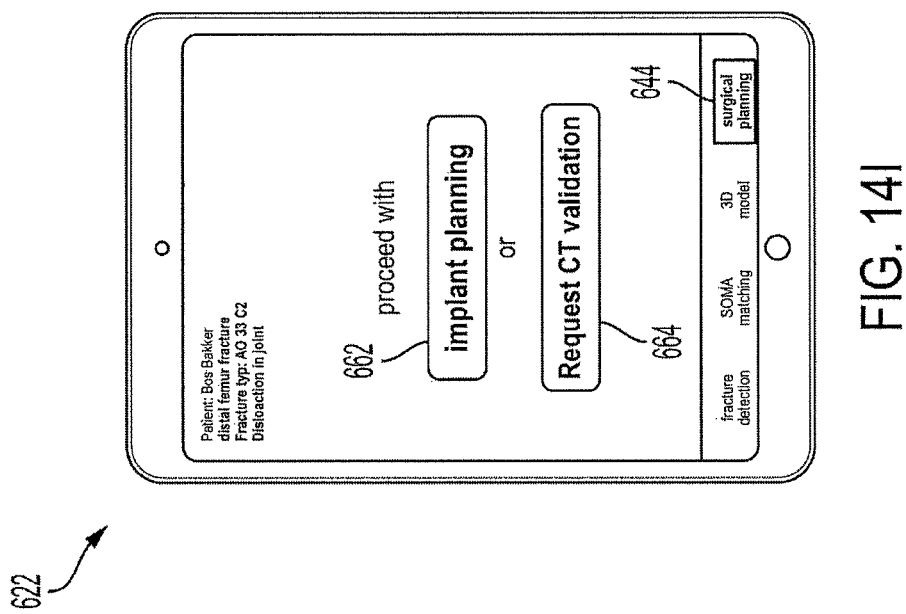
Figure 15:
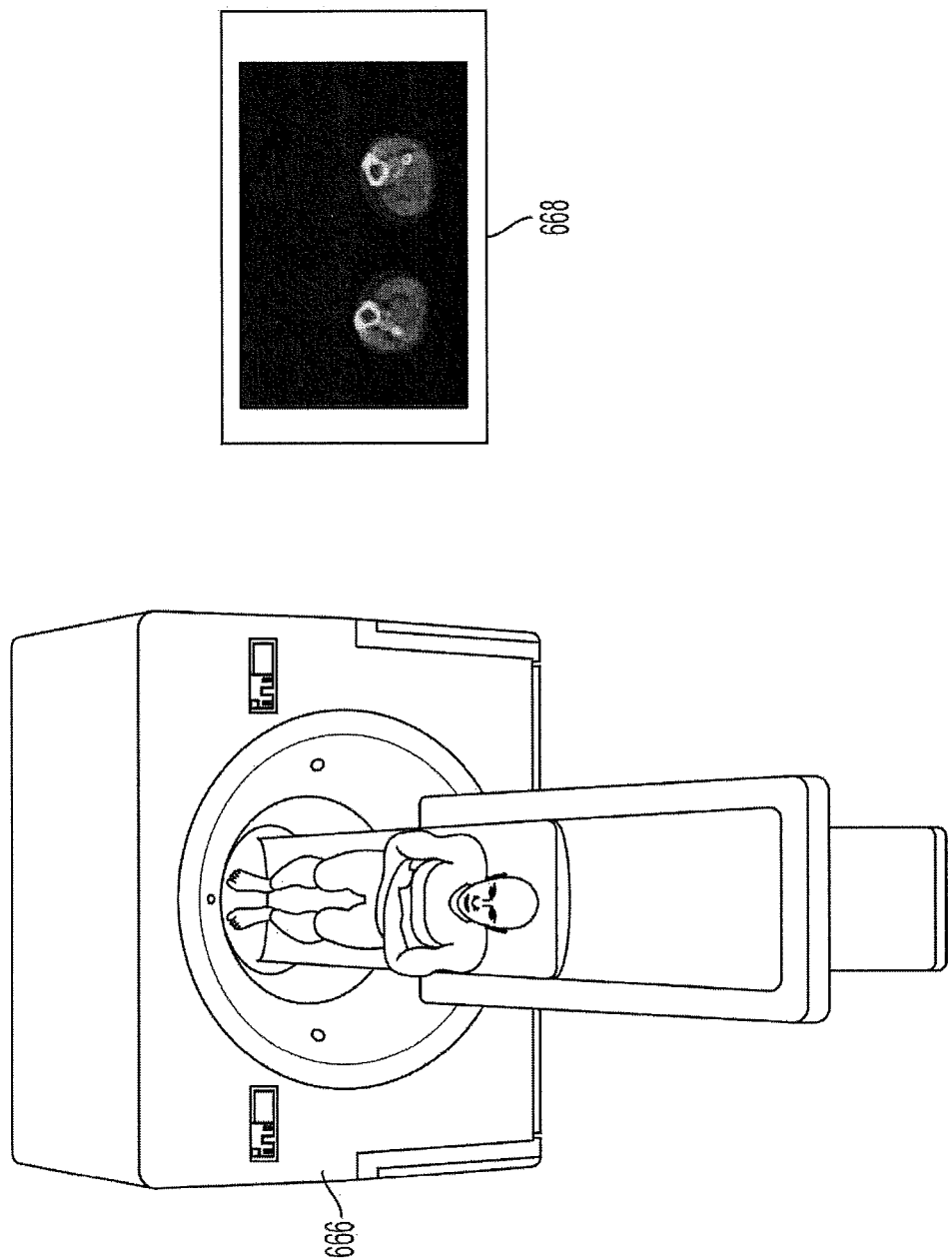
FIG. 15 is a perspective view of a CT scan imaging system of the surgical procedure work flow shown in FIG. 12.

FIGS. 14G and 14H show 3D modeling routine 642 of fracture diagnostic support 622. A 3D view of the patient's femur and tibia from imaging data 612 is generated on tablet 624 when 3D modeling routine 642 is activated. The 3D view includes image visualization options such as a transparency-opacity selector to adjust the visibility of the 3D model. The 3D model depicting the bone fracture can now be virtually reduced by sliding a cursor between the non reduced 658 and reduced 660 positions displayed on tablet 624. Once an operator has completed these steps utilizing fracture diagnostic support system 622, the operator can proceed to virtual implant planning 662 or request a CT validation 664 as shown in FIG. 14I. If the operator choses to validate the implant planning with a CT scan, the patient will undergo a CT scan utilizing a CT scanning machine 666 to generate CT scan data 668 as shown in FIG. 15. CT scan data 668 can then be utilized to perform, verify and validate implant planning.

Figure 16A:
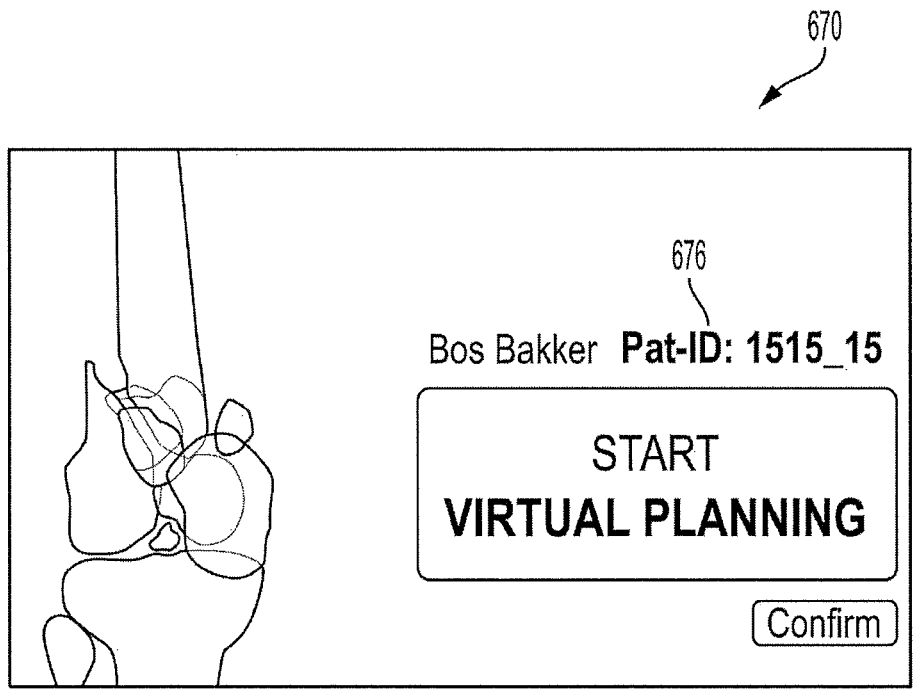
FIGS. 16A-N are schematic views showing various stages of a virtual surgical planning of the surgical procedure work flow shown in FIG. 12.
Figure 16B:
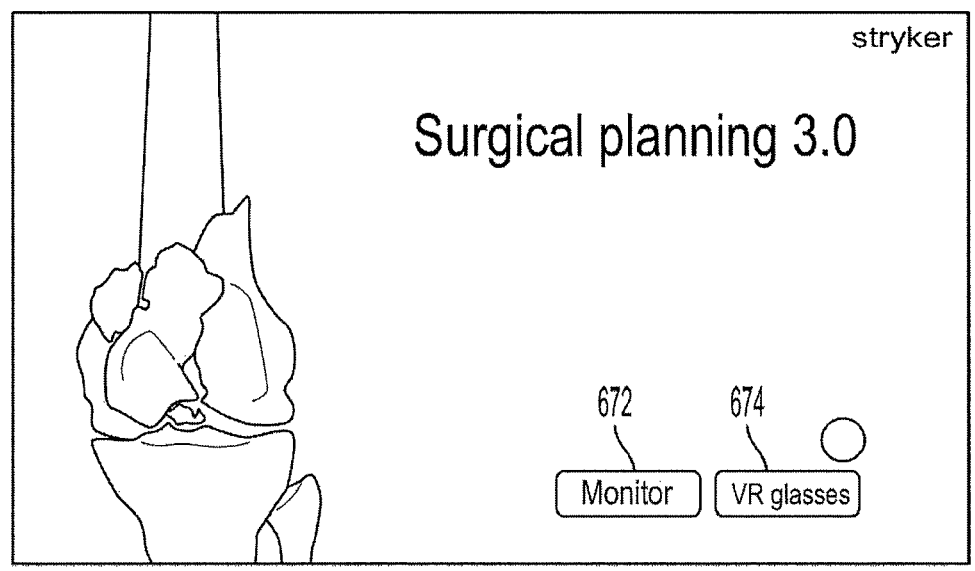
Figures 16C, 16D:
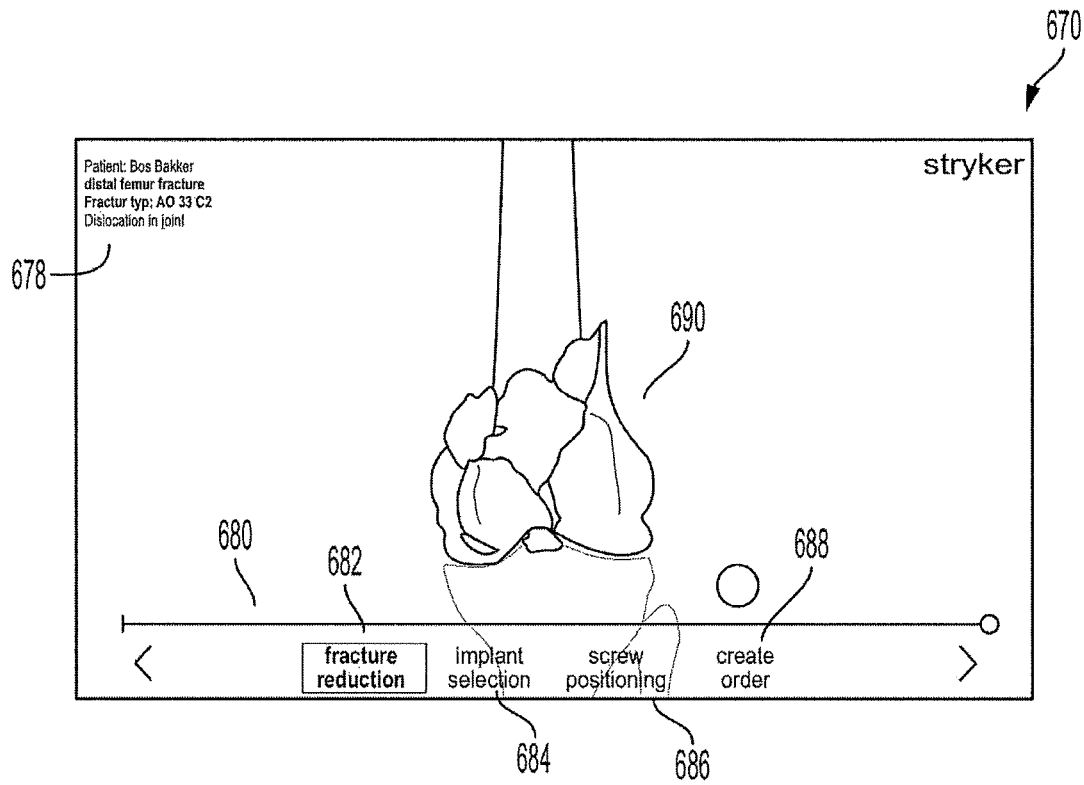
Figure 16E:
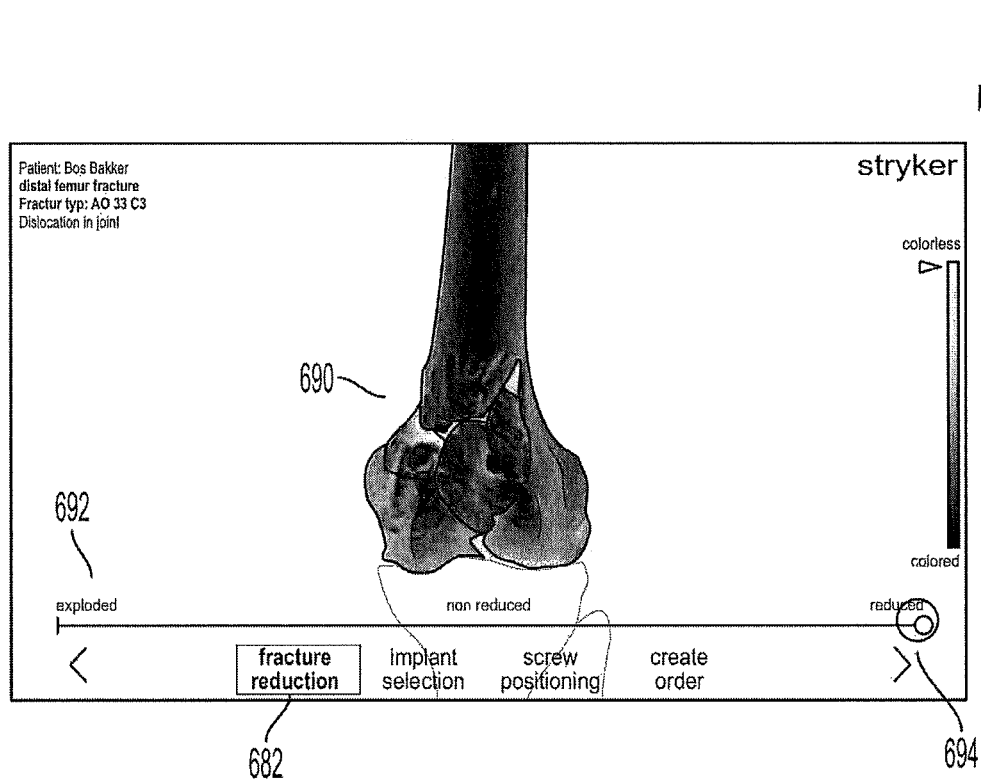
Figure 16F:
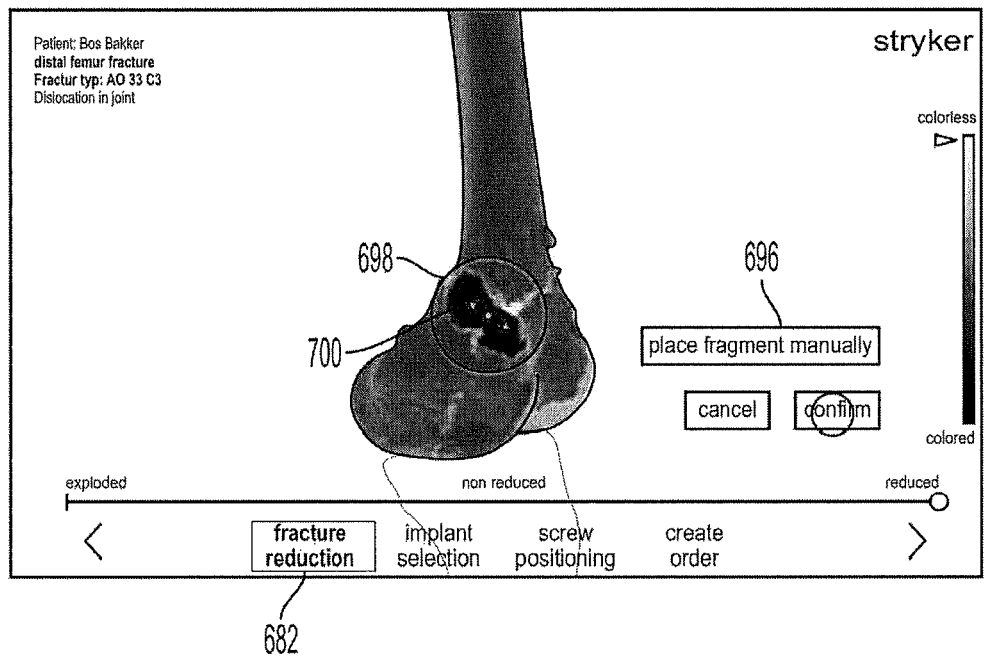
Figure 16G:
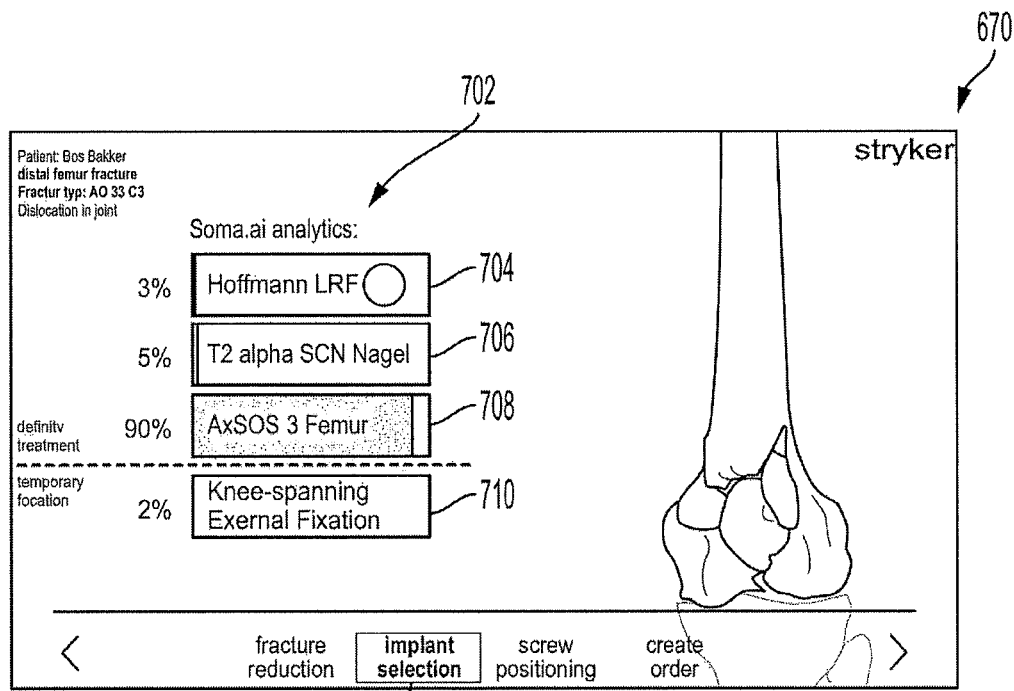
Figure 16H:
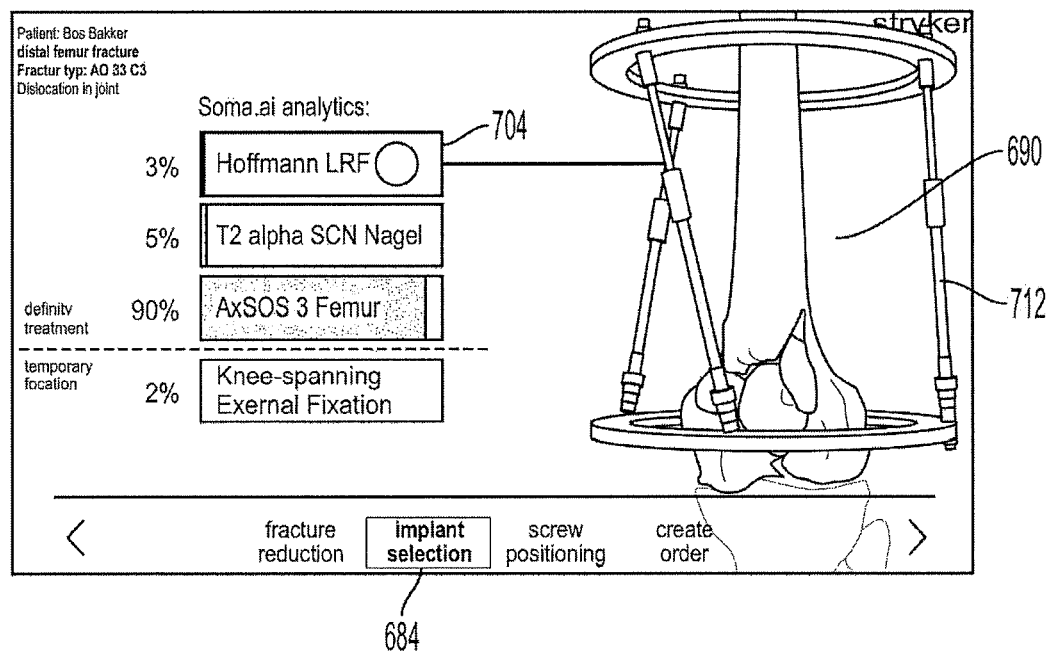
Figure 16I:
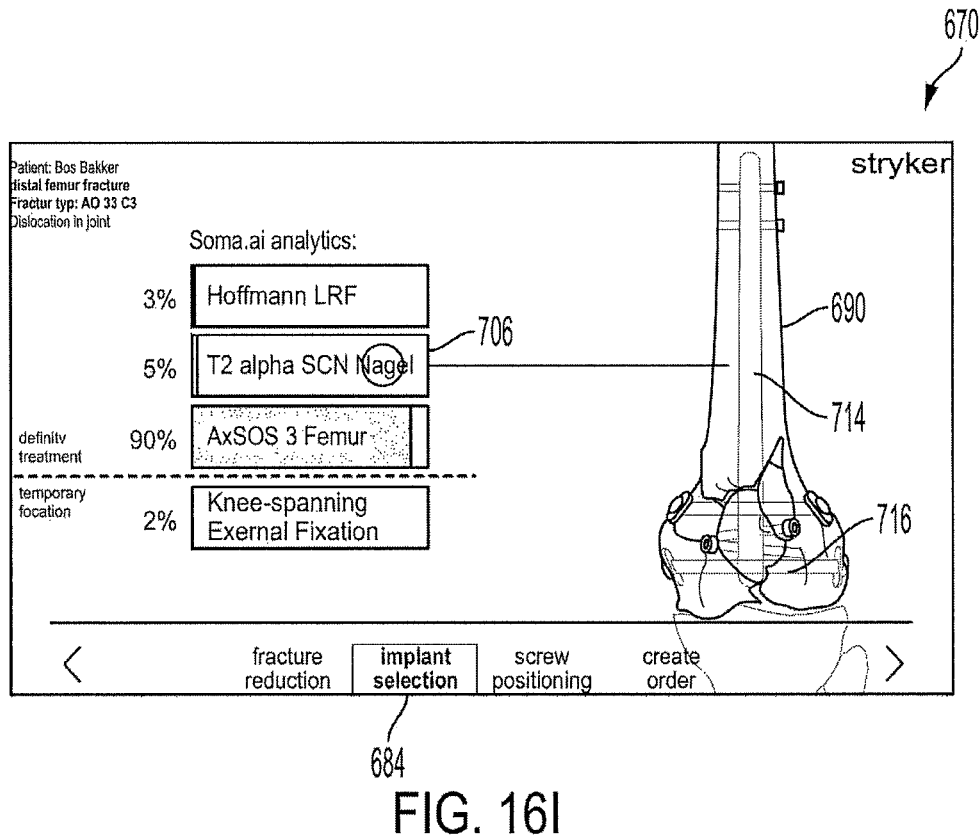
Figure 16J:
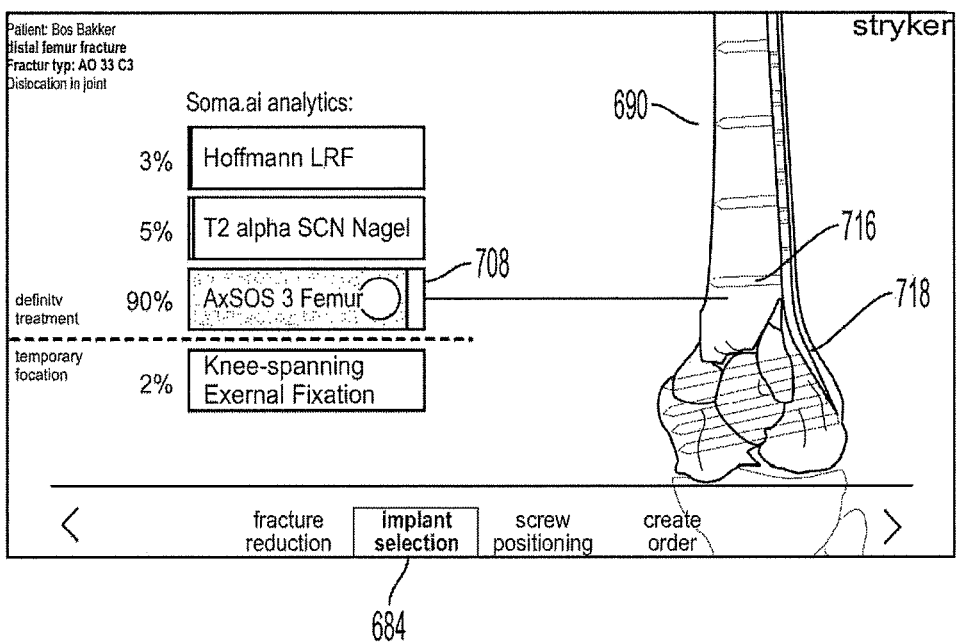
Figure 16K:
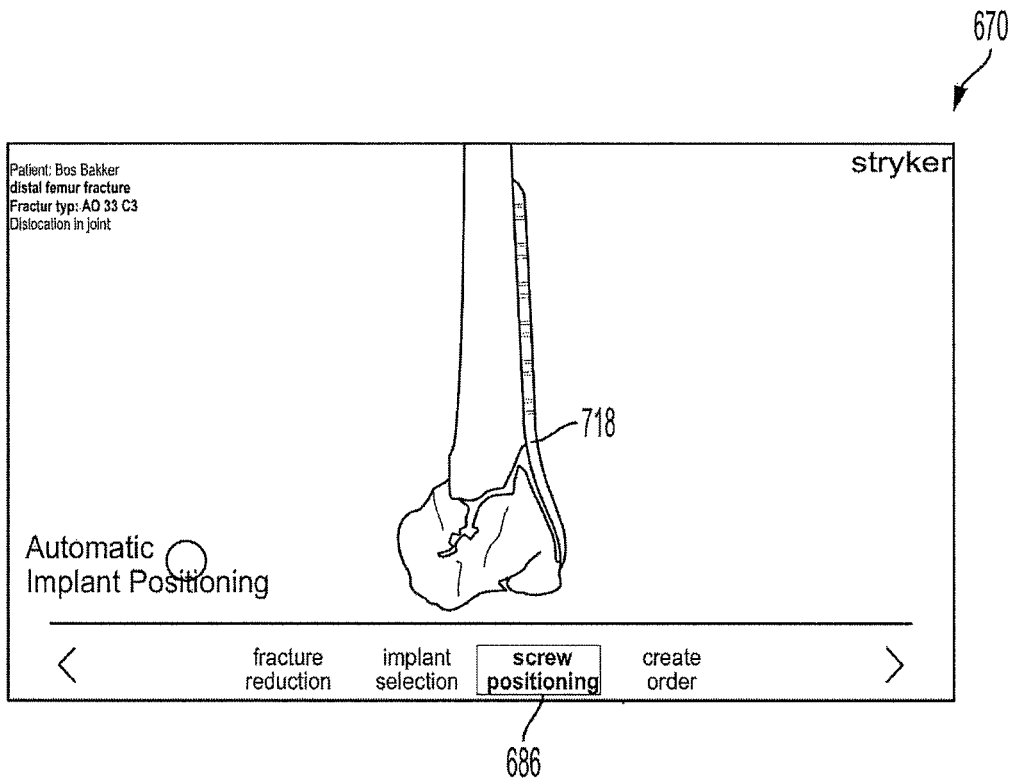
Figure 16L:
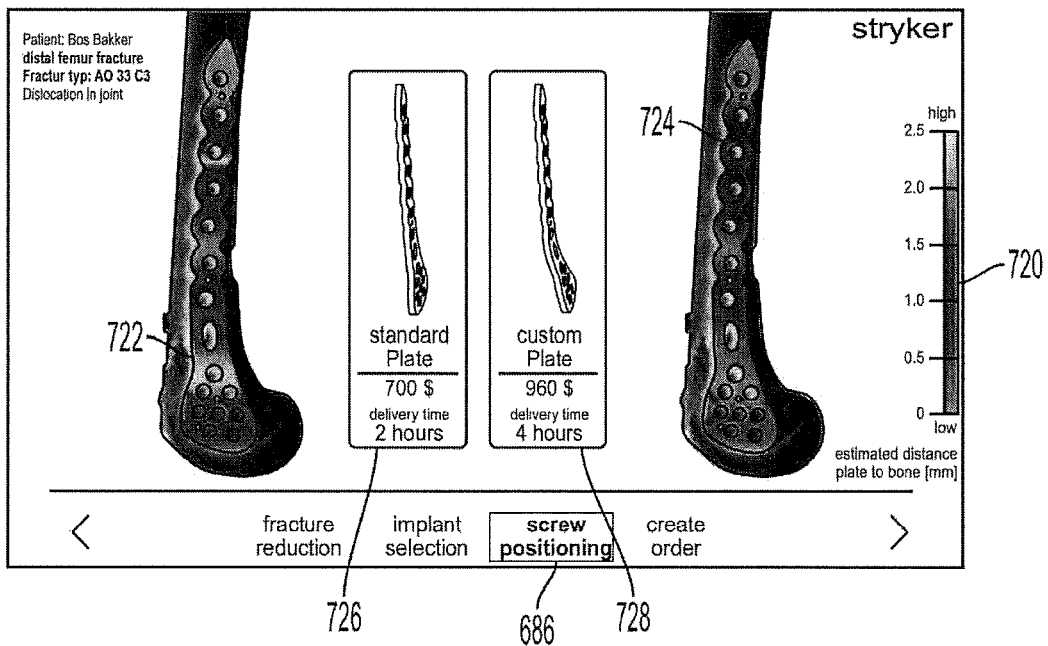
Figure 16M:
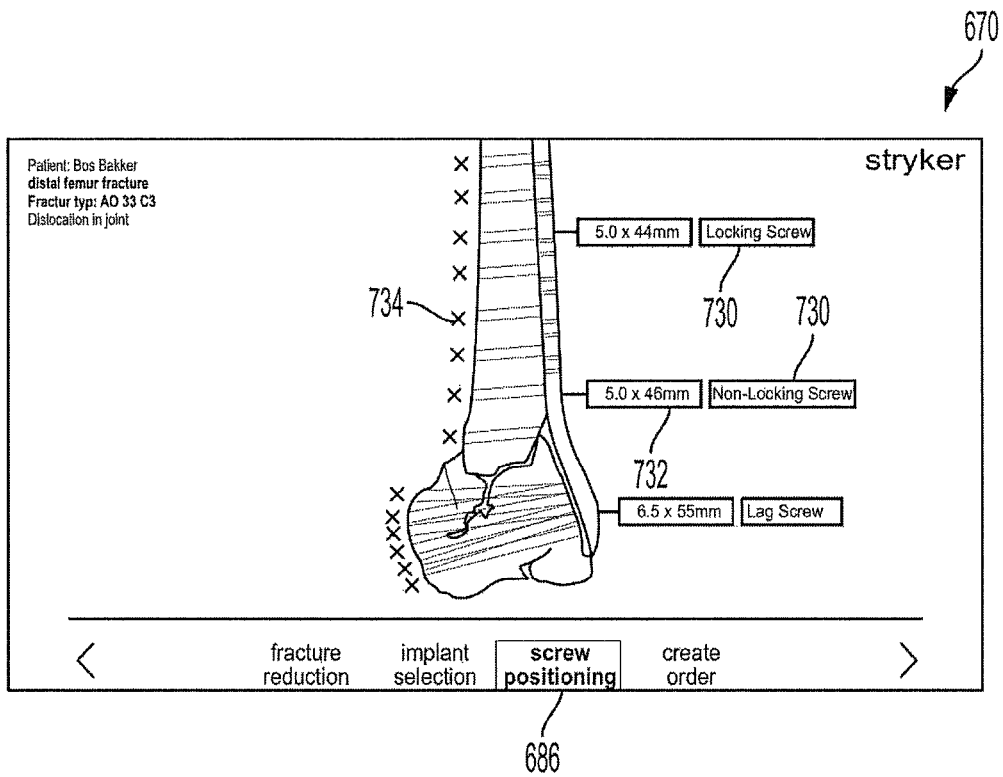
Figure 16N:
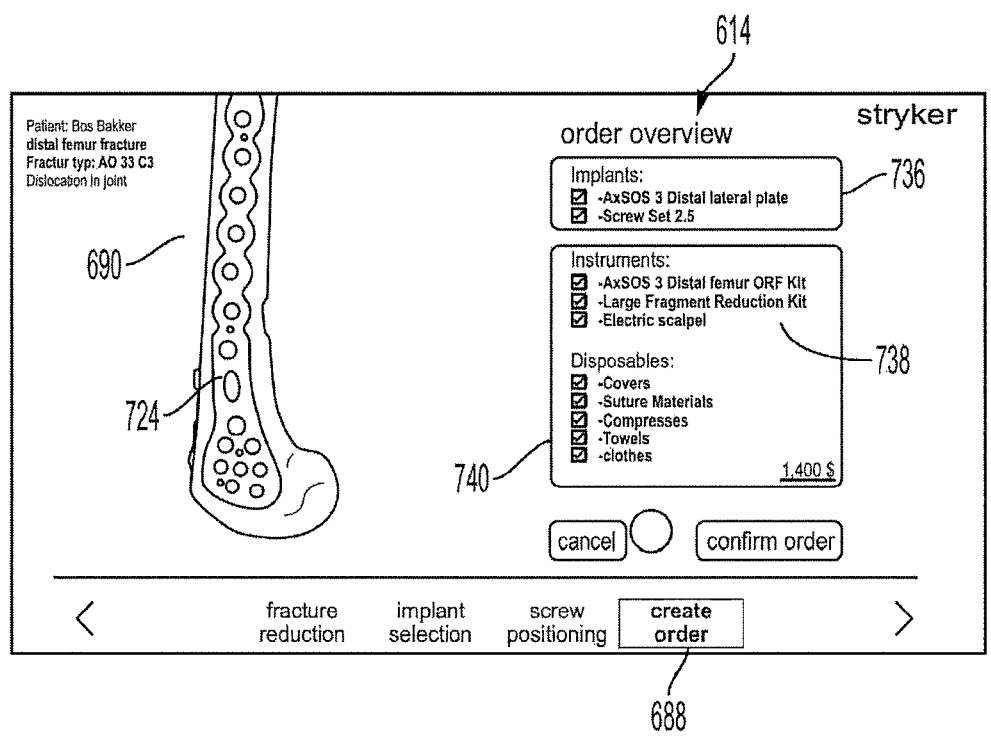

Referring now to FIGS. 16A-16N, there are shown schematic views of various stages of a virtual surgical planning 670 of the surgical procedure work flow 600. Virtual surgical planning 670 can be performed on a monitor 672 or with virtual reality glasses 674 as shown in FIG. 16B. Other image augmentation techniques such as augmented reality techniques or any combinations of these techniques can also be used in to perform virtual surgical planning 670. Patient specific identification 676 is displayed on a display device such as tablet 624. Virtual surgical planning 670 includes a virtual implant planning menu 680 as shown in FIG. 16C. Virtual implant planning menu 680 includes a fracture reduction routine 682, an implant selection routine 684, a fastener positioning routine 686, and an order generation routine 688.

FIGS. 16C-16D show fracture reduction routine 682 of virtual surgical planning 670. A 3D bone model 690 is displayed on table 624 as shown in FIG. 16C. 3D bone model 690 can be exploded using an explode routine 692 showing the various fractured bone fragments as shown in FIG. 16D. An image visualization selector 656 allows an operator to vary the color level of 3D bone model 690 for optimal viewing. Activating a reducing routine 694 reduces the 3D bone model 690 to allow an operator to visualize fracture reduction as best shown in FIG. 16E. If desired, a bone fragment 698 can be manually moved by an operator using direction arrows 700 to place and properly position bone fragment 698 as shown in FIG. 16F.

Referring now to FIGS. 16G-I, there is shown implant selection routine 684 of virtual planning system 670. Implant selection routine 684 includes an implant selection menu 702 providing an external fixation system selection 704, a nailing system selection 706, a plating system selection 708, and a temporary fixation system selection 710 as shown in FIG. 16G. FIG. 16H shows an implant selection routine 684 with an external fixation system selection 704. A limb reconstruction frame 712 is virtually positioned around 3D bone model 690 allowing an operator to select a limb reconstruction frame to match the patient's specific needs and position the same. Activating nailing system selection 706 provides the operator with an intramedullary nail 714 positioned in 3D bone model 690 as shown in FIG. I. Fasteners 716 to secure intramedullary nail 714 to 3D bone model 690 is displayed on tablet 624 allowing for virtual implant planning. Similarly, activating plating system selection 708 provides a virtual 3D representation of a bone plate 718 with associated fasteners 716 as best shown in FIG. 16J.

FIGS. 16K-M show fastener positioning routine 686 of virtual planning system 670. Fastener positioning routine 686 can be activated after virtual implant selection described above. As shown in FIG. 16K, bone plate 718 is properly positioned on 3D bone model 690. Activating the fastener positioning routine 686 generates a virtual standard bone plate 722 and a virtual custom bone plate 724 as shown in FIG. 16L. Standard bone plate 722 and custom bone plate 724 are overlaid on a plate-to-bone scale 720. Plate-to-bone scale 720 denotes the distance between the bone and the bone-contacting surface of bone plates 722, 724. The plate-to-bone scale allows an operator to decide if standard bone plate 722 or a custom bone plate 724 is required. Virtual planning system 670 displays the estimated cost and time required to generate the standard bone plate 726 and custom bone plate 728. Hence, an operator can factor cost and time to select the appropriate bone plate. In this embodiment, a custom bone plate 724 is selected and displayed on 3D bone model 690. Fastener positioning routine 686 allows an operator to select fastener location 734, fastener type 730 and fastener length 732. As shown in FIG. 16M, an operator can select fastener location by clicking on fastener location 734 to activate or deactivate fasteners. Selected fasteners can be oriented by clicking and dragging fastener location 734 to desired positions on tablet 624. Fastener selection can be made by clicking on fastener type 730 to select a locking screw, non-locking screw, bolt, etc. Fastener length can be varied by clicking on fastener length 732 to ensure proper fastener penetration into bone.

Referring now to FIG. 16N, there is shown the final step in generating surgical kit order 614 based on virtual implant planning system 670. Surgical kit order 614 includes implant selection 736, instrument list 738 and disposable item list 740. Implant selection 736 can include implant type and associated fasteners. Instrument list 738 can include all associated instruments required for conducting the surgical procedure to implant the selected implant. Disposable item list 740 can include disposables such as towels, suture materials, compresses, etc. to conduct the required surgical procedure. Thus, surgical kit order 614 contains a complete kit of all required material to perform the required surgical procedure.

Figure 17:
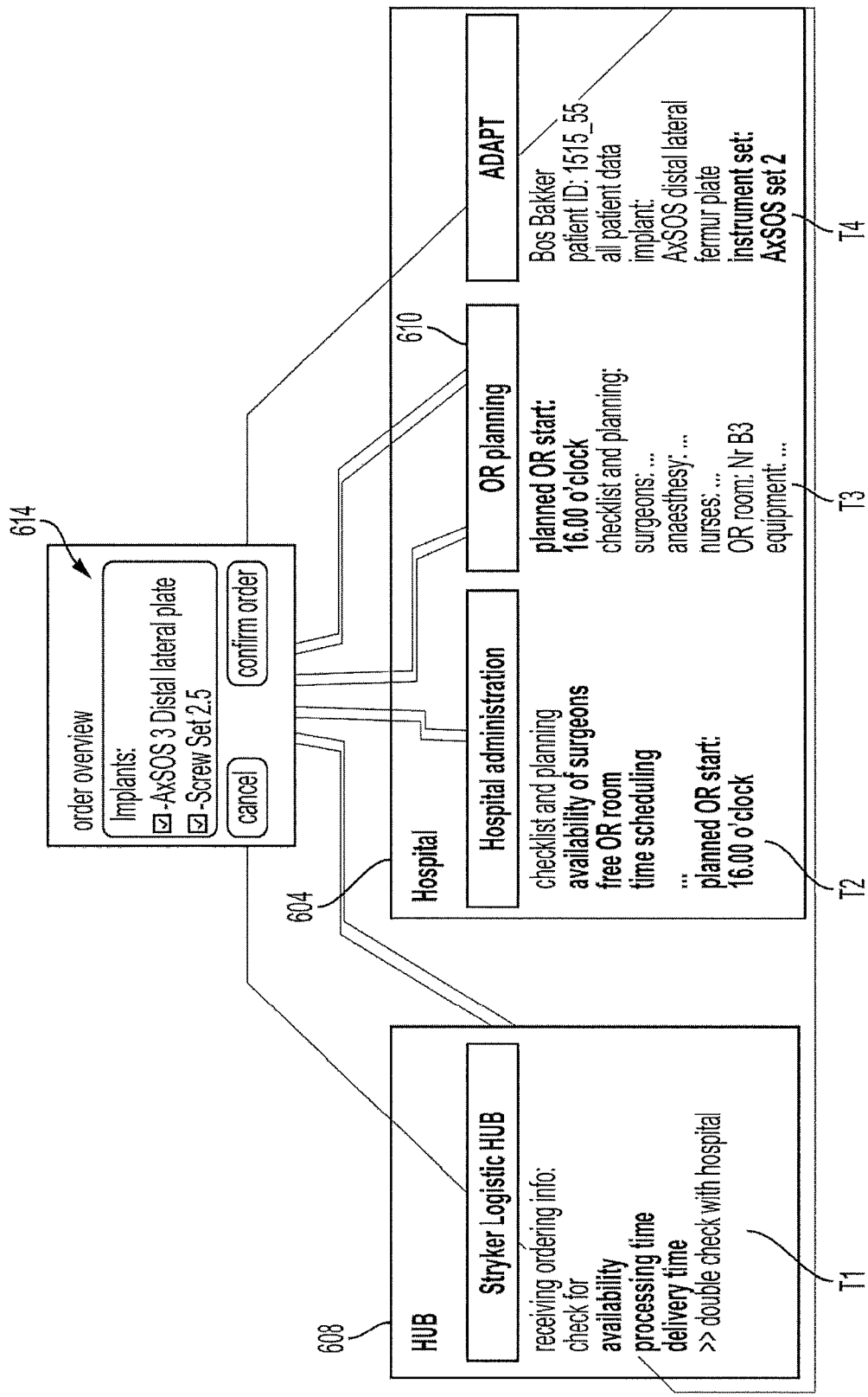
FIG. 17 is a schematic view showing an exemplary timeline of the surgical procedure work flow shown in FIG. 12.

Surgical kit order 614 and virtual planning system 670 information is transmitted to logistical hub 608, hospital 604, and operating room 610 as shown in FIG. 17. Logistical hub 608 receives surgical kit order 614 at time T1 and commences preparation of same. Hospital 604 receives virtual planning details at time T2 to schedule surgeon availability and an operating room to perform the surgical procedure. As shown in FIG. 17, surgical procedure is schedule at time T3 in operating room 610. Patient information and preoperative virtual planning information is transmitted to an intraoperative surgical assistance system 822 at time T4 as more fully described below. Scheduling of these events can be optimized in response to the urgency and criticality of surgery, operation room availability, surgeon availability, and time to prepare surgical kit 616.

Figure 18:
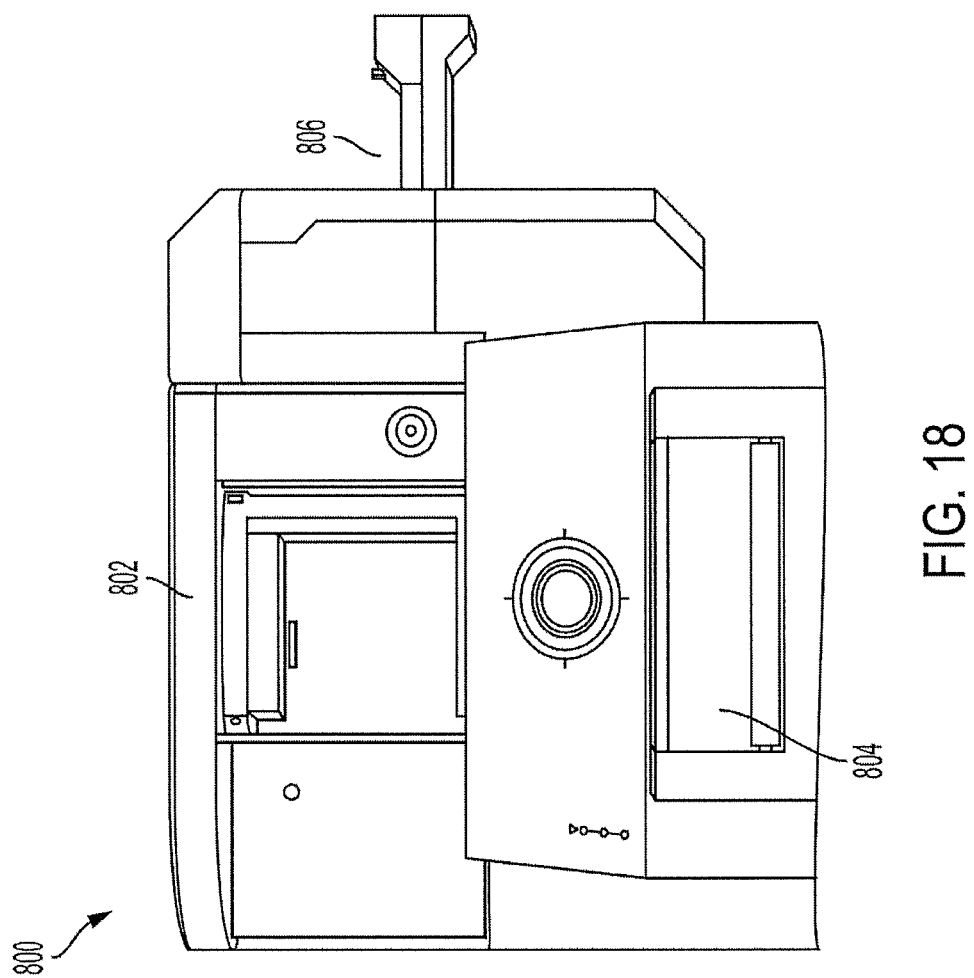
FIG. 18 is a front view of an implant customization apparatus of the surgical procedure work flow shown in FIG. 12.
Figure 19A:
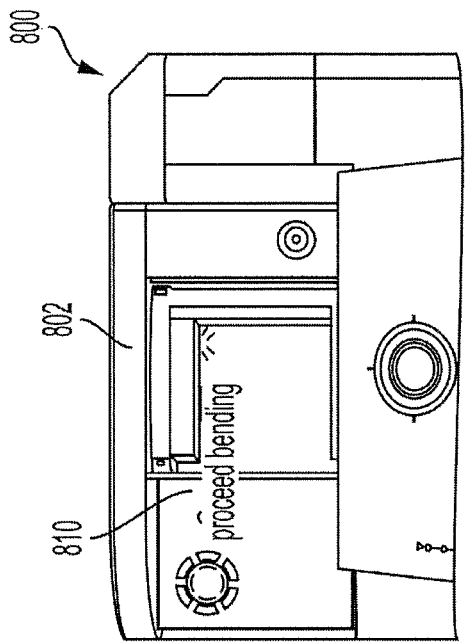
FIGS. 19A-C are schematic views showing various stages of implant customization using implant customization apparatus shown in FIG. 18.
Figure 19B:
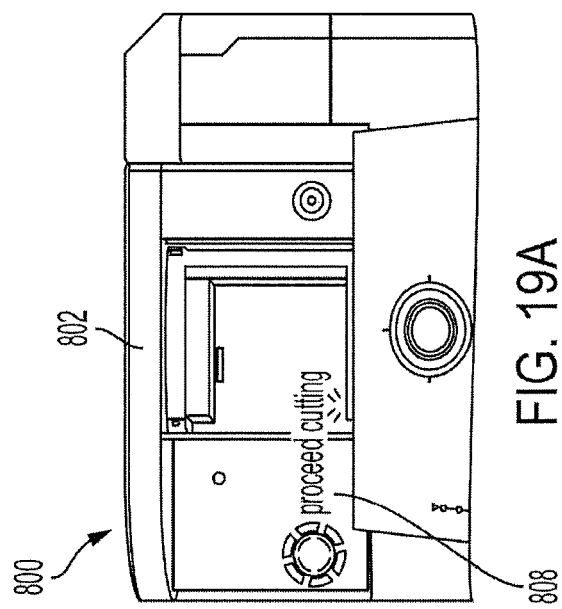
Figure 19C:
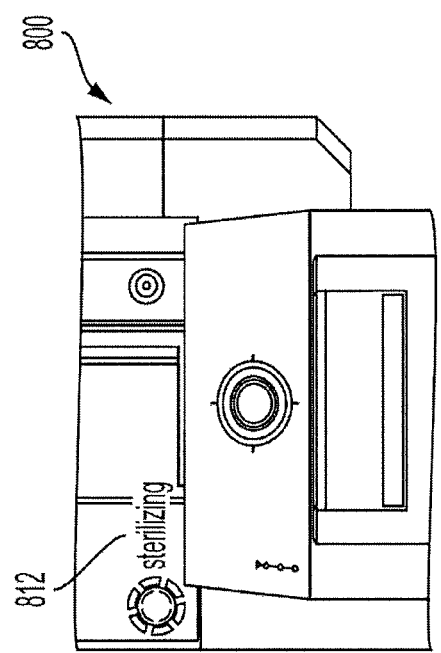

An automatic implant manager 800 located in logistical hub 608 is shown in FIG. 18. Automated implant manager 800 includes an implant processing portion 802, and an implant sterilization portion 804. An implant blank delivery mechanism 806 is configured to select a suitable implant blank from an implant blank library (not shown) and deliver the same to automated implant manager 800. Implant delivery mechanism 806 is configured to select implant blank to minimize material wastage and machining requirements. Implant processing portion 802 includes a cutting mechanism 802 to perform cutting operations as shown in FIG. 19A. A bending mechanism 810 is included in the processing portion 802 to perform bending operations as shown in FIG. 19B. Examples of implant bending machines can in include implant bending machines 900, 1000, 1100 and 1200 discussed above. Automatic implant manager 800 includes an implant sterilization mechanism 812 to sterilize the customized implant blank as shown in FIG. 19C. Sterilization mechanism can include ethylene oxide (ETO), hydrogen peroxide, autoclaving, dry heating or other means. A sterilization progress display on automatic implant manager 800 indicates the time required for and the status of the sterilization process.

Figure 20B:
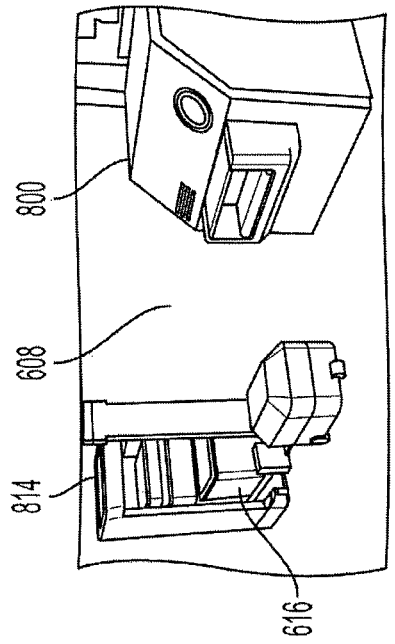
FIGS. 20A-H are schematics views showing steps for preparing a surgical kit for the surgical procedure work flow shown in FIG. 12.
Figure 20C:
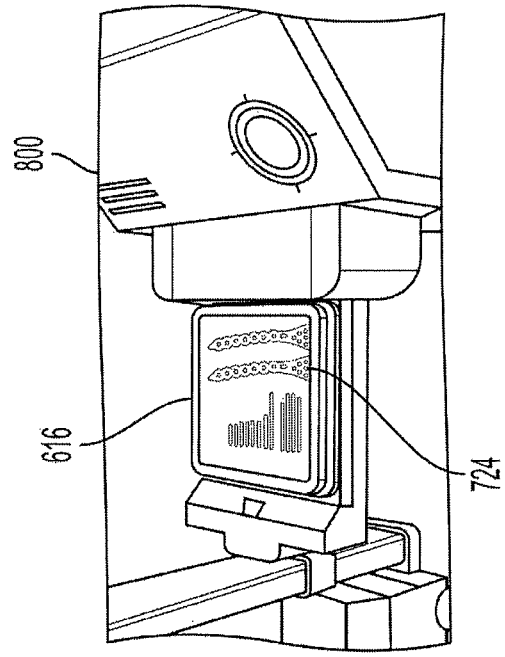
Figure 20A:
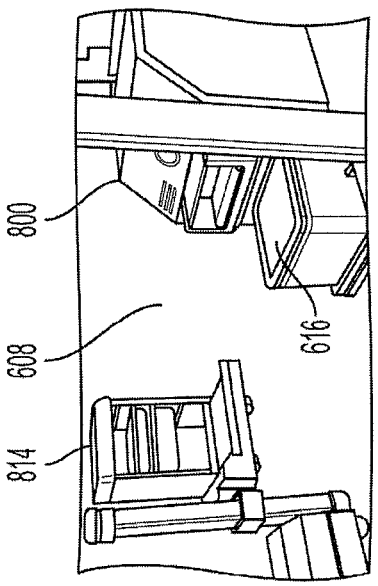
Figure 20D:
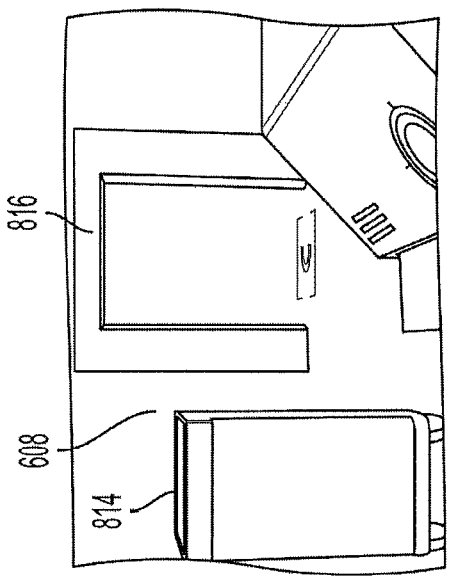
Figure 20E:
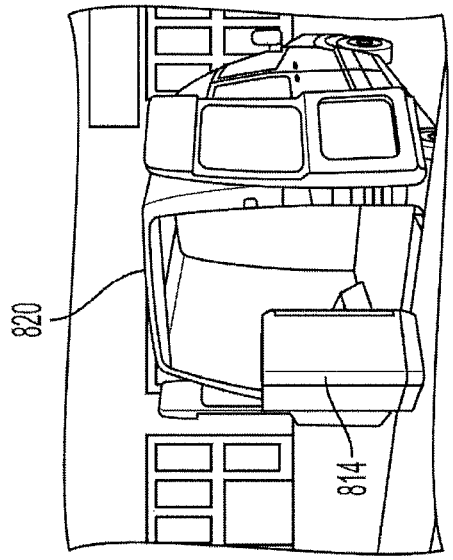
Figure 20F:
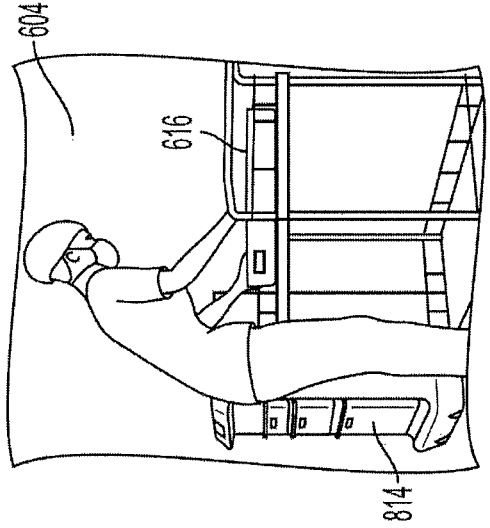
Figure 20H:
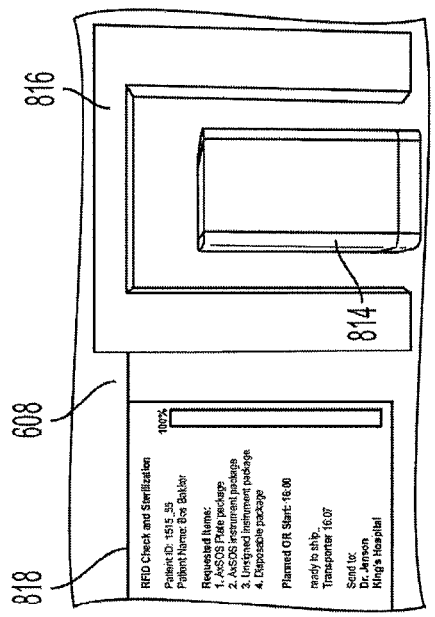
Figure 20G:
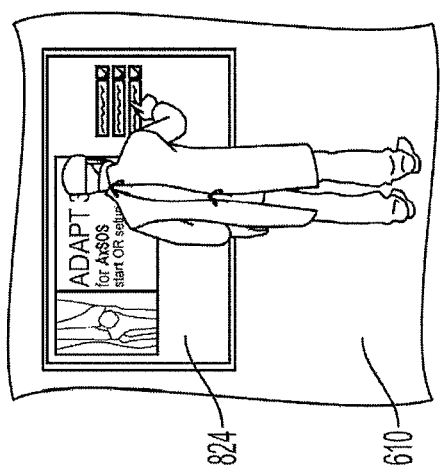

Referring now to FIGS. 20A-H, there is shown schematic steps for preparing surgical kit 616. As described above, surgical kit 616 includes implant 724, fasteners, surgical instruments and disposables. The fully prepared surgical kit 616 is placed in a surgery-ready-cart 814 as shown in FIGS. 20A and B. Surgery-read-cart 814 is configured to provide a sterile environment to maintain the sterility of surgical kit 616 contents. Surgical kit 616 includes a radio-frequency identification (RFID) tag to identify and track the surgical kit. An RFID scanner 816 located in logistical hub 608 scans surgical kit 616 as surgery-ready-cart 814 departs the logistical hub as shown in FIGS. 20D and E. Surgery-ready-cart 814 is transported to hospital 604 by suitable means to ensure sterility of the surgical kit as shown in FIG. 20F. Upon arrival at hospital 604, an operator removes surgical kit 614 from surgery-ready-cart 814 as shown in FIG. 20G while ensuring sterility of the surgical kit contents. Sterility of surgical kit 616 may be maintained by the manner disclosed in U.S. patent application Ser. No. 14/819,092, the disclosure of which is hereby incorporated by reference herein. The sterile surgical kit 616 is transported to operating room 610 as shown in FIG. 20H. Reusable items that are not utilized during surgery can be loaded back on surgery-ready-cart 814 or any other means and delivered back to logistical hub 608 to be reused.

Figure 21A:
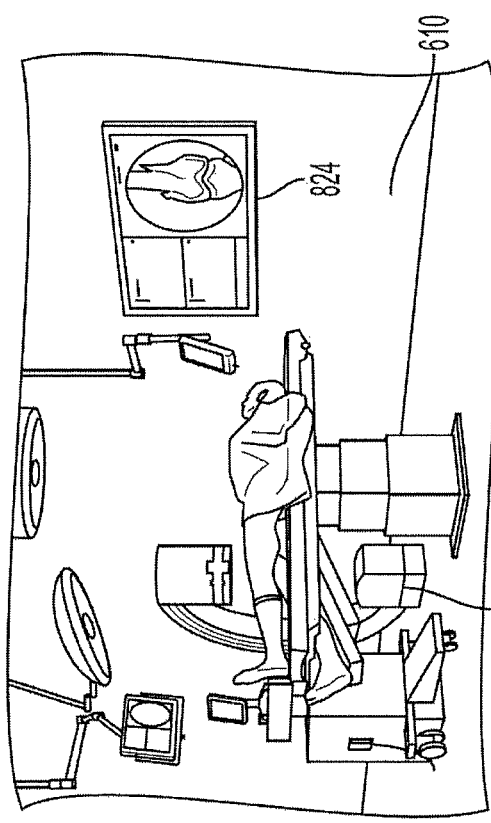
FIGS. 21A-C are schematic views showing various stages of intraoperative planning and assistance of the surgical procedure work flow shown in FIG. 12.
Figure 21B:
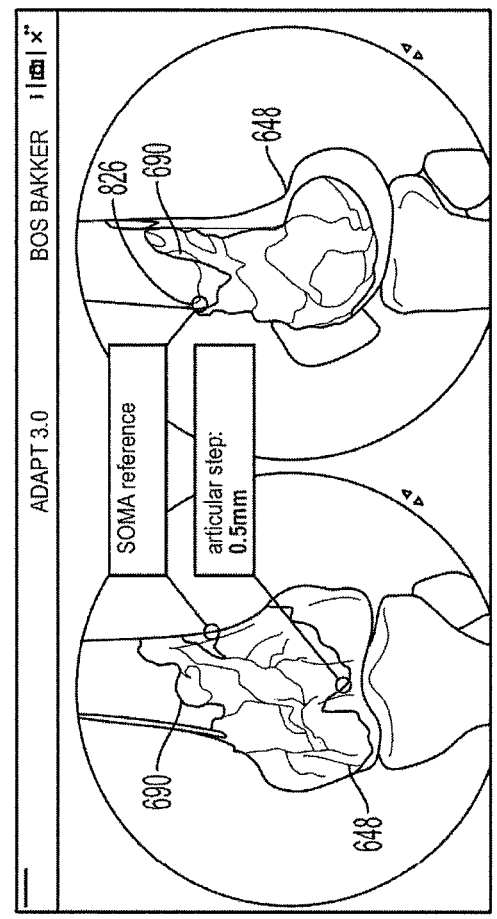
Figure 21C:
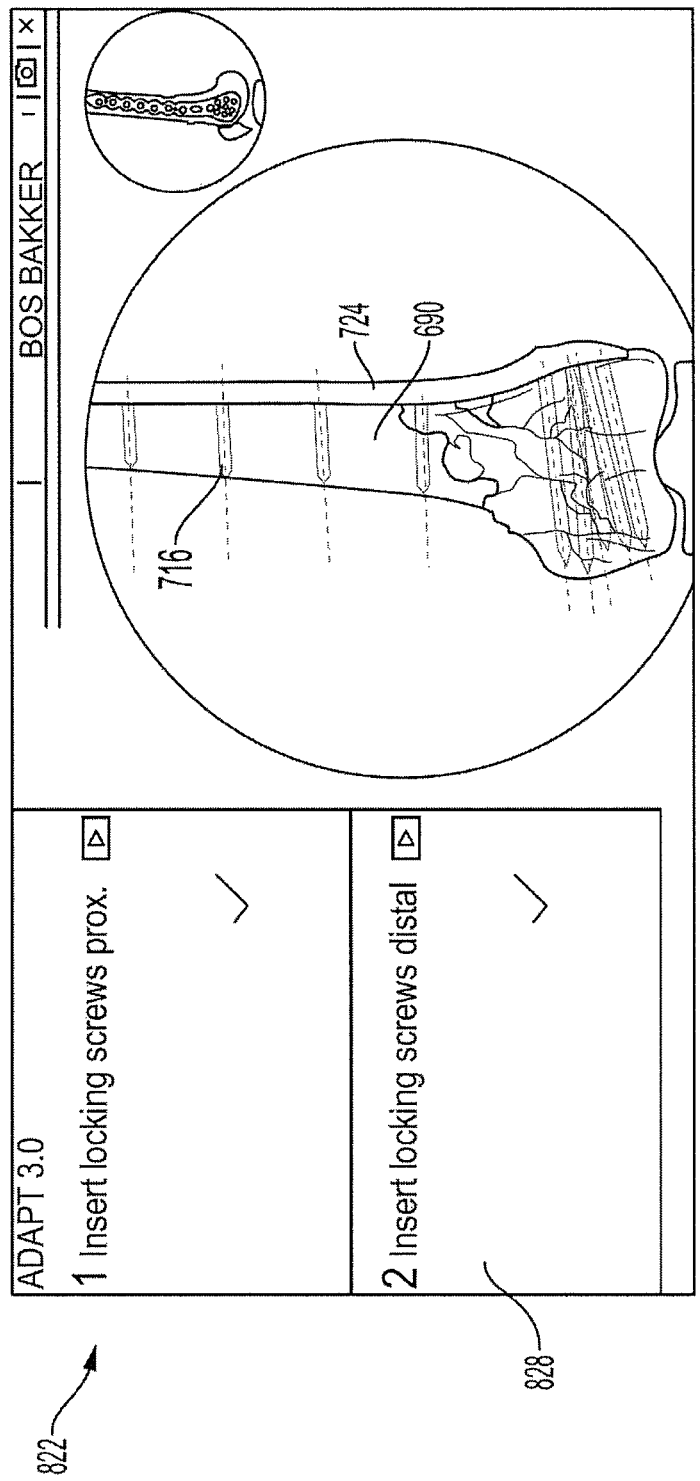
Figure 22:
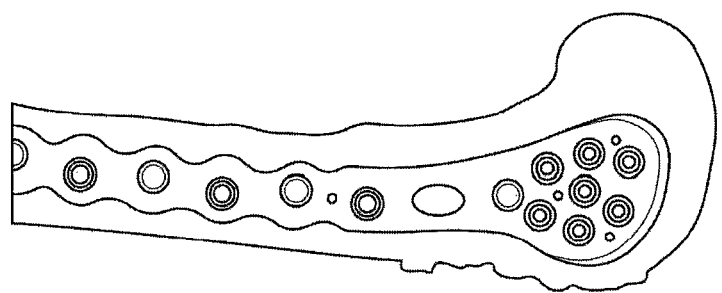
FIG. 22 is a schematic view of a post-operative checklist of the surgical procedure work flow shown in FIG. 12.

FIGS. 21A-C show schematic view of stages of intraoperative surgical assistance utilizing intraoperative surgical assistance system 822. An intraoperative assistance display 824 is provided in operating room 610 as show in FIG. 21A. A posterior-anterior and medial-lateral view of 3D bone model 690 is overlaid with the database generated bone model outline 648 as shown in FIG. 21B to intraoperatively assist the surgeon. A surgical procedure checklist 828 depicting the various surgical steps can be displayed on display 824 to assist surgeon as shown in FIG. 21C. Upon completion of the surgical procedure, a summary of surgical procedure work flow 600 is generated and stored as show in FIG. 22.

Figure 23B:
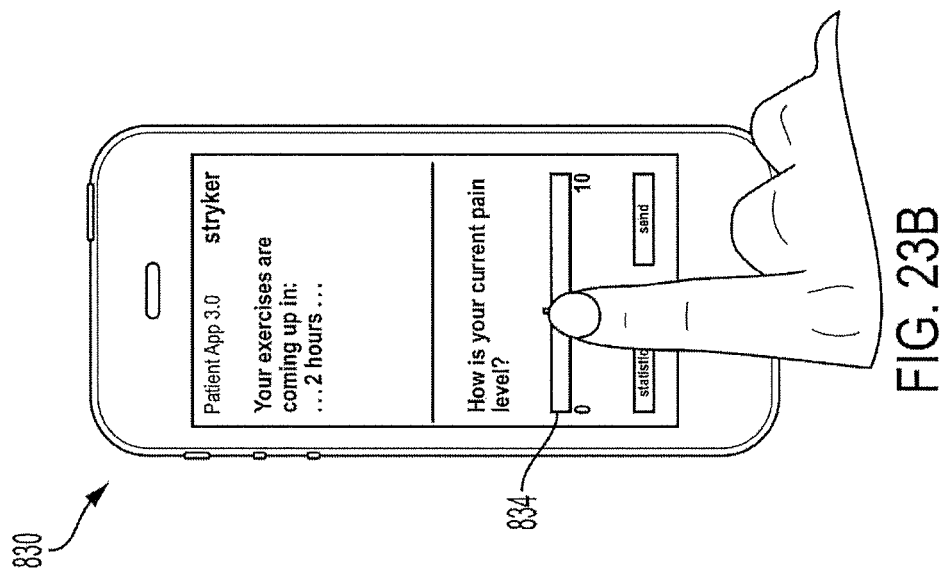
FIGS. 23A and B are schematic views showing a patient application used in conjunction with the surgical procedure work flow shown in FIG. 12.
Figure 23A:
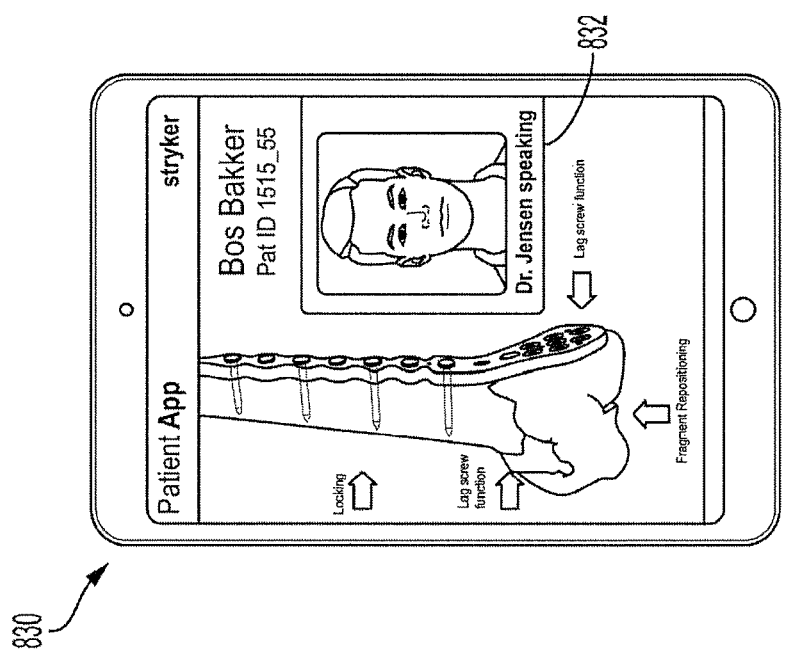

Surgical procedure work flow 600 can include a mobile application 830 for communication between the patient and the surgeon as shown in FIGS. 23A and B. For example, the surgeon can inform and educated the patient about the surgical procedure (FIG. 23A). The patient can conveniently provide feedback regarding recovery after surgery using mobile application 830 as shown in FIG. 23B. Communication utilizing mobile application 830 can be synchronized with surgical procedure work flow 600 to conveniently maintain all records related to the surgical procedure.

While the example described above is directed to a surgical procedure involving a bone plate to treat a fracture, the surgical work flow of the present invention can be utilized for any surgical procedures.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the paragraphs below. Moreover, the foregoing disclosure should be taken by way of illustration rather than by way of limitation as the present invention is defined in the examples of the numbered paragraphs, which describe features in accordance with various embodiments of the invention, set forth in the paragraphs below.

The invention claimed is:

1. A surgical system for generating patient-specific implants comprising:
a flexible template that can be manipulated on a target body region to correspond to a patient-specific implant, and
a customization apparatus comprising a storage portion having one or more implant blanks, an implant customization portion, and an interface configured to receive information from the flexible template, the storage portion and the implant customization portion being disposed within a body of the customization apparatus,
wherein the information is used by the implant customization portion to intraoperatively or preoperatively manipulate the implant blank to a patient-specific implant in a surgical care environment.

2. The surgical system of claim 1, wherein the information includes shape and dimensional information of the flexible template.

3. The surgical system of claim 1, wherein the storage portion and the implant customization portion are sterile such that the implant blanks remain sterile during and after customization.

4. The surgical system of claim 1, wherein the implant customization portion includes a bending mechanism such that the implant blank is bent to form the patient-specific implant.

5. The surgical system of claim 4, wherein the bending mechanism includes a series of movable elements, a distal end of at least one element configured to translate by an actuator such that the distal ends of the movable elements define a profile of the patient-specific implant.

6. The surgical system of claim 5, wherein the bending mechanism includes a first row of movable elements on a first side of the patient-specific implant and a second row of movable elements on a second side of the patient-specific implant.

7. The surgical system of claim 6, wherein the bending mechanism includes a translatable frame attached to any of the movable elements and the patient-specific implant.

8. The surgical system of claim 1, wherein the implant customization portion includes a cutting mechanism such that the implant blank is cut to form the patient-specific implant.

9. The surgical system of claim 1, wherein the implant customization portion includes a bending mechanism and a cutting mechanism such that the implant blank is cut and bent to form the patient-specific implant.

10. The surgical system of claim 1, wherein the interface allows input from an operator to modify the information.

11. The surgical system of claim 1, wherein the customization apparatus further includes a display device to display a virtual patient-specific implant generated by the information.

12. The surgical system of claim 1, wherein the patient-specific implant is a bone plate.

13. A method for implant customization in a surgical care environment comprising the steps of:
positioning a flexible template on a target body region;
manipulate the flexible template from a first condition to a second condition such that the flexible template in the second condition conforms to the target body region;
sending information of the flexible template in the second condition to a customization apparatus;
selecting an implant blank from a storage portion of the customization apparatus based on the information;
customizing the implant blank using an implant customization portion of the customization apparatus to manipulate the implant blank to a patient-specific implant based on the information,
wherein the storage portion and the implant customization portion are disposed within a body of the customization apparatus, the customization apparatus being located in a surgical care environment such that the customization is performed intraoperatively or preoperatively.

14. The method of claim 13, wherein the customization apparatus includes a bending mechanism and the step of customizing the implant blank is performed by bending the implant blank with the bending mechanism to generate the patient-specific implant based on the information.

15. The method of claim 13, wherein the customization apparatus includes a cutting mechanism and the step of customizing the implant blank is performed by cutting the implant blank with the cutting mechanism to generate the patient-specific implant based on the information.

16. The method of claim 13, wherein the customization apparatus includes a bending mechanism and a cutting mechanism and the step of customizing the implant blank is performed by bending and cutting the implant blank by the bending mechanism and the cutting mechanism respectively to generate the patient-specific implant based on the information.

17. The method of claim 13, wherein the step of sending information of the flexible template in the second condition includes send information shape and dimensional information of the flexible template in the second condition to the customization apparatus.

18. The method of claim 13, wherein the target body region is a fractured bone and the information includes information related to a virtual bone reduction of the fractured bone.

19. The method of claim 18, wherein the patient-specific implant is a patent-specific bone plate that corresponds to the virtual bone reduction information.

20. The method of claim 13, wherein the step of selecting an implant blank is performed by evaluating the information to minimize customization of the selected implant blank to generate the patient-specific implant.

* * * * *